US006839762B1

(12) United States Patent
Yu et al.

(10) Patent No.: US 6,839,762 B1
(45) Date of Patent: *Jan. 4, 2005

(54) ULTRASOUND INFORMATION PROCESSING SYSTEM AND ULTRASOUND INFORMATION EXCHANGE PROTOCOL THEREFOR

(75) Inventors: Zengpin Yu, Palo Alto, CA (US); Shengtz Lin, Cupertino, CA (US); Eddy Ye, San Jose, CA (US); Thomas P. Neff, Newark, CA (US)

(73) Assignee: U-Systems, Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,197

(22) Filed: May 16, 2000

Related U.S. Application Data

(63) Continuation-in-part of application No. 09/449,095, filed on Nov. 24, 1999, which is a continuation-in-part of application No. 09/224,635, filed on Dec. 31, 1998.

(51) Int. Cl.[7] ............................................. G06F 15/16
(52) U.S. Cl. ..................................... 709/230; 709/232
(58) Field of Search .............................. 709/230–232, 709/203, 204; 600/437, 447, 445; 345/483, 853, 564; 714/47; 367/135

(56) References Cited

U.S. PATENT DOCUMENTS

| | | | |
|---|---|---|---|
| 4,853,875 A | | 8/1989 | Brown |
| 5,295,485 A | | 3/1994 | Shinomura et al. |
| 5,353,220 A | * | 10/1994 | Ito et al. ..................... 600/437 |
| 5,483,963 A | | 1/1996 | Butler et al. |
| 5,492,125 A | | 2/1996 | Kim et al. |

(List continued on next page.)

OTHER PUBLICATIONS

An Object–Oriented Framework for High–Performance Electronic . . . —Schmidt, Harrison; sunsite.bcc.bilkent.edu.tr/pub/languages/c++/class–libraries/ACE/ACE–documentation/SPIE–95.ps.gz.*

Cardiac Wall Tracking Using Doppler Tissue Imaging (DTI).—Cohen, Pajany, Pellerin . . . ; www.ceremade.dauphine.fr/~cohen/mypapers/icip96dti.ps.gz.*

(List continued on next page.)

Primary Examiner—Thong Vu
(74) Attorney, Agent, or Firm—Cooper & Dunham LLP

(57) ABSTRACT

An ultrasound information processing system comprises a plurality of ultrasound devices coupled to a high-speed serial ultrasound information bus, wherein each ultrasound device comprises a program for communicating with other ultrasound devices according to an ultrasound information exchange protocol (UIEP). The UIEP is a lightweight, connection-oriented protocol adapted to efficiently transfer ultrasound information among different devices on the ultrasound information bus. Each ultrasound device comprises an application layer program for performing an ultrasound function, as well as a lower protocol layer program for receiving and sending data across the ultrasound information bus according to a high-speed serial bus standard that provides both isochronous and asynchronous data delivery. The ultrasound information exchange protocol (UIEP) program is adapted to receive a communication request from the application layer, open a connection-oriented communication session with the requested ultrasound device, and transfer ultrasound information through the lower protocol layer and across the ultrasound information bus to the requested device. Advantageously, any ultrasound device manufacturer provided with the UIEP program may readily generate application layer code capable of communicating with other manufacturers' ultrasound devices across the ultrasound information bus, without requiring specific knowledge of the internal structure of the other manufacturers' devices or of the specific frame/packet structure of the UIEP/lower layer protocols themselves.

38 Claims, 11 Drawing Sheets

U.S. PATENT DOCUMENTS

| | | | | |
|---|---|---|---|---|
| 5,555,534 A | * | 9/1996 | Maslak et al. | 367/135 |
| 5,590,658 A | | 1/1997 | Chiang et al. | |
| 5,603,323 A | | 2/1997 | Pflugrath et al. | |
| 5,609,485 A | * | 3/1997 | Bergman et al. | 434/262 |
| 5,630,101 A | | 5/1997 | Sieffert | |
| 5,709,206 A | | 1/1998 | Teboul | |
| 5,709,209 A | | 1/1998 | Friemel et al. | |
| 5,715,823 A | | 2/1998 | Wood et al. | |
| 5,778,177 A | | 7/1998 | Azar | |
| 5,795,297 A | | 8/1998 | Daigle | |
| 5,838,592 A | | 11/1998 | Spratt | |
| 5,842,473 A | * | 12/1998 | Fenster et al. | 600/445 |
| 5,851,186 A | * | 12/1998 | Wood et al. | 600/437 |
| 5,853,367 A | | 12/1998 | Chalek et al. | |
| 5,885,218 A | | 3/1999 | Teo et al. | |
| 5,920,317 A | * | 7/1999 | McDonald | 345/853 |
| 5,964,708 A | * | 10/1999 | Freeman et al. | 600/447 |
| 5,997,478 A | | 12/1999 | Jackson et al. | |
| 6,079,033 A | * | 6/2000 | Jacobson et al. | 714/47 |
| 6,101,407 A | | 8/2000 | Groezinger | |
| 6,159,150 A | * | 12/2000 | Yale et al. | 600/437 |
| 6,262,749 B1 | * | 7/2001 | Finger et al. | 345/564 |
| 6,547,730 B1 | * | 4/2003 | Lin et al. | 600/437 |

OTHER PUBLICATIONS

An Object–Oriented Client–Server System for . . . —Scheinine . . . (1998); sunsite.informatik.rwth–aachen.de/Publications/CEUR–WS/Vol–12/./080.ps.*

James A. Zagzebski, *Essentials of Ultrasound Physics* (1996) (title page and table of contents).

Texas Instruments, Inc., http://www.ti.com.

Sheldon, *The Encyclopedia of Networking,* McGraw–Hill (1997).

* cited by examiner

ULTRASOUND INFORMATION PROCESSING SYSTEM AND ULTRASOUND INFORMATION EXCHANGE PROTOCOL THEREFOR

CROSS-REFERENCE TO RELATED APPLICATIONS

This application is a continuation-in-part of U.S. patent application Ser. No. 09/449,095, entitled "Scalable Real-Time Ultrasound Information Processing System," filed Nov. 24, 1999, which is a continuation-in-part of U.S. patent application Ser. No. 09/224,635, entitled "Ultrasound Information Processing System," filed Dec. 31, 1998, both assigned to the assignee of the present invention. The above two disclosures are hereby incorporated by reference into the present disclosure.

FIELD

This patent specification relates to the field of ultrasound information processing systems. In particular, the present invention relates to an architecture for a flexible, high-performance, reduced cost, and upgradable ultrasound information processing system and a standardized protocol for allowing ready interoperability of ultrasound devices within and across such systems.

BACKGROUND

Ultrasound imaging systems are advantageous for use in medical diagnosis as they are non-invasive, easy-to-use, and do not subject patients to the dangers of electromagnetic radiation. An ultrasound imaging system transmits sound waves of very high frequency (e.g., 2 MHz to 10 MHz) into the patient and processes echoes reflected from structures in the patient's body to form two dimensional or three dimensional images. Many ultrasound information processing algorithms are known in the art, for example, echo mode ("B mode") processing algorithms, motion mode ("M mode") processing algorithms, Doppler shift echo processing algorithms, color flow mode processing algorithms, and others.

Present day ultrasound imaging systems typically comprise a host computer or processor that is responsible for user interface control, image display, and overall system control. These systems further typically comprise one or more peripheral devices, such as ultrasound scanner/probe assemblies and digital signal processors, that perform specific ultrasound information processing functions. As described in Ser. No. 09/224,635, supra, prior art ultrasound architectures generally use custom, proprietary connections and protocols for transferring information among the different ultrasound system elements. Connections between the ultrasound system elements are typically implemented using hardware parallel busses that, while at least partially conforming to an industrial standard such as the VME standard, are otherwise uniquely adapted for the specific hosts, scanners, digital signal processors, etc. being provided by the specific system manufacturer. Ultrasound algorithms, such as those embodied in the scan sequences of an ultrasound scanner, are typically stored in custom hardware memory maps within that scanner, and can only be changed or upgraded if the specific memory map architecture of that specific scanner is known.

Accordingly, in the case of the prior art architectures supra, it is either impossible or impractical to substitute a first manufacturer's ultrasound component (such as a host, scanner, or digital signal processor) into a second manufacturer's ultrasound processing system. As a result, it is less feasible for the purchaser of an ultrasound processing system to easily upgrade to newer, better, and/or less expensive ultrasound components that are being continually developed in the industry. It is also less feasible for the purchaser to upgrade to new ultrasound information processing algorithms or scanning strategies as they are developed in the industry.

Accordingly, it would be desirable to provide an ultrasound communication method that, upon being followed by a plurality of ultrasound component manufacturers, would allow for the construction of an ultrasound information processing system that can readily use ultrasound components or algorithms from different manufacturers or different models.

It would be further desirable to provide an ultrasound communication method in which a first ultrasound device may change internal parameters of a second ultrasound device without requiring knowledge of the specific internal memory map of the second ultrasound device.

It would be further desirable to provide an ultrasound communication method that is based on a serial bus architecture for allowing flexibility, scaleability, and plug-and-play simplicity in an ultrasound information processing system.

It would be still further desirable to provide an ultrasound communication method that properly synchronizes ultrasound devices coupled to the serial bus.

It would be even further desirable to provide an ultrasound communication method that permits ready communications between any two devices connected to the serial bus, without requiring their application layer programs to contain detailed serial bus communications instructions.

SUMMARY

In accordance with a preferred embodiment, an ultrasound information processing system is provided comprising a plurality of ultrasound devices coupled to a high-speed serial ultrasound information bus, each ultrasound device comprising a program for communicating with other ultrasound devices according to an ultrasound information exchange protocol. The ultrasound information exchange protocol represents a standard, lightweight, connection-oriented protocol adapted for efficient transfer of ultrasound information among different devices on the ultrasound information bus.

Each ultrasound device in the ultrasound information processing system comprises an application layer program for performing an ultrasound function and a lower protocol layer program for receiving and sending data across the ultrasound information bus. The lower protocol layer program is preferably a standard, off-the-shelf program that implements IEEE 1394/1995, USB, Fibre Channel, or other high-speed serial bus protocol providing both isochronous and asynchronous data delivery. An ultrasound information exchange protocol (UIEP) program is adapted to receive a communication request from the application layer, open a connection-oriented communication session with the requested ultrasound device, and transfer ultrasound information between the devices during the communication session. Advantageously, any ultrasound device manufacturer provided with the UIEP program may readily generate application layer code capable of communicating with other manufacturers' ultrasound devices across the ultrasound information bus, without requiring specific knowledge of the internal structure of the other manufacturers' devices or of the specific frame/packet structure of the UIEP/lower layer protocols themselves.

In accordance with a preferred embodiment, the UIEP protocol comprises a ultrasound transport protocol (UTP) layer for providing a reliable, connection-oriented data delivery service between ultrasound ports of different ultrasound devices. The UIEP protocol further comprises an ultrasound service protocol (USP) for providing an interface between the UTP layer and the application layer. The UIEP protocol provides for a bulk image data type whose frames are transmitted isochronously between ultrasound devices, and an asynchronous command data type whose frames are transmitted asynchronously between ultrasound devices. Separate ports are provided on each ultrasound device for handling the bulk image data and the asynchronous command data.

In a preferred embodiment, ultrasound scanning devices conforming to the UIEP protocol comprise at least one memory block that may be loaded and managed by a remote host device, wherein the remote host device is not required to have knowledge of the specific memory architecture of the scanning device. In particular, the UIEP provides for communication and management of memory addresses in a logical address space, wherein physical memory addresses in the scanning device are derived locally by combining (e.g. adding) logical address offsets with a corresponding hardware address.

According to a preferred embodiment, the UIEP compensates for the pipelined nature of serial bus communications by allowing proper inter-device synchronization as bulk image data is transferred and processed. An ultrasound source device, such as a scanner, generates image data in accordance with (a) intrinsic parameters that are included within each bulk data frame, together with (b) extrinsic parameters that are not included within each bulk data frame. However, for each bulk data frame, the host device requires knowledge of both the intrinsic and extrinsic parameters to properly process the frame. According to a preferred embodiment, the scanner attaches an ultrasound state identifier to each bulk image frame, which is then used by the host device to locate the correct set of extrinsic parameters for processing that frame. Sets of extrinsic parameters and their corresponding ultrasound state identifiers are communicated between the scanner and host using their asynchronous command ports or broadcast ports as the extrinsic parameters are varied. Synchronization, i.e. proper matching of the bulk data frames with the proper set of extrinsic parameters, is thereby preserved as the extrinsic parameters are varied.

DETAILED DESCRIPTION

Figure 1:
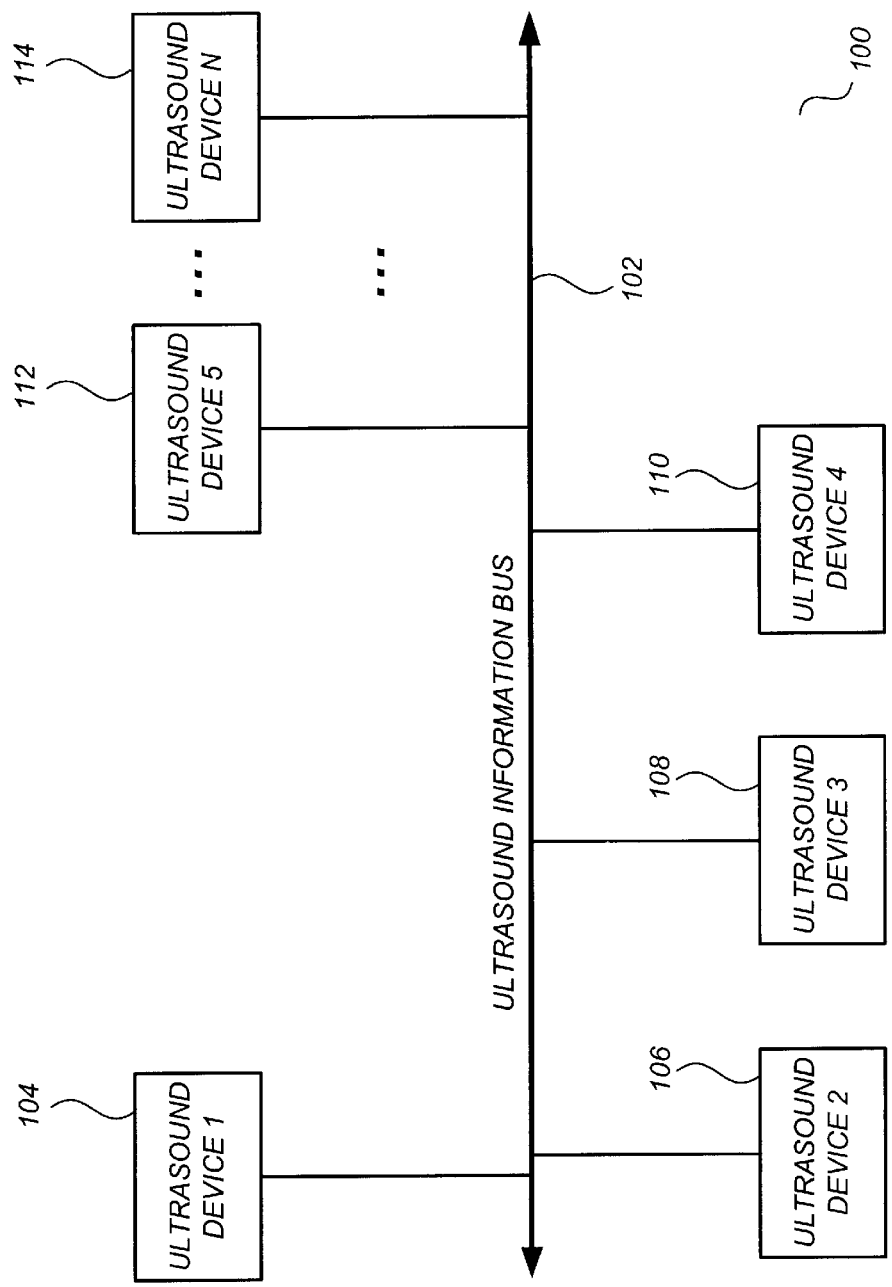
FIG. 1 shows an ultrasound information processing system in accordance with a preferred embodiment.

FIG. 1 shows an ultrasound information processing system 100 in accordance with a preferred embodiment. Ultrasound information processing system 100 comprises an ultrasound information bus 102 and a plurality of ultrasound devices 104–114 coupled thereto. The ultrasound information bus 102 is a high-speed serial bus operating in accordance with any of a variety of high-speed serial bus protocols, such as IEEE 1394/1995 ("Firewire"), USB, Fibre Channel, or others. In general, the high-speed serial bus protocol may be any protocol that provides for both isochronous and asynchronous data transfer, as described in Ser. No. 09/224,635, supra.

The ultrasound devices 104–114 shown in FIG. 1 may be any of a variety of device combinations for achieving a desired ultrasound information processing functionality. For example, ultrasound device 104 may be a host computer for providing overall system control, user display, user input, and image processing functions. Ultrasound device 106 may be a scanner/probe assembly for generating raw ultrasound image data. Ultrasound devices 108–114 may be any of a variety of auxiliary ultrasound devices. By way of example and not by way of limitation, such auxiliary ultrasound devices may include: specialized signal processing devices; ultrasound storage devices; auxiliary displays; hot-swappable backup devices; auxiliary system control devices, or generally any device performing a functionality useful to an ultrasound information processing system.

Although physical coupling between each ultrasound device and the ultrasound information bus 102 is indicated in FIG. 1, it would be within the scope of the preferred embodiments for one or more of the ultrasound devices to wirelessly communicate with the ultrasound information bus 102. Additionally, although the ultrasound information bus 102 of FIG. 1 is shown as a local area network, it would be within the scope of the preferred embodiments for ultrasound information bus 102 to be implemented as a wide area network coupling a plurality of local area networks using, for example, ATM or frame relay links. Thus, the physical implementations of ultrasound information bus 102 may take a variety of forms, provided that high-speed isochronous data transfer and asynchronous data transfer is permitted between any two of the ultrasound devices 104–114.

According to a preferred embodiment in which the features and advantages of the architecture and protocol described infra are used, a system purchaser may insert upgraded, additional, or replacement ultrasound devices from any manufacturer into the ultrasound information processing system by simply "plugging them in" to the ultrasound information bus 102. As an example, a purchaser may have purchased a "bare bones" system comprising only a host and a scanner from a first ultrasound manufacturer a while ago, but may now wish to include a new, specialized, intermediate processing device that has just been released by a second ultrasound manufacturer. According to the preferred embodiments, the user may (a) plug the intermediate processing device into the ultrasound information bus 102, (b) redirect the output of the scanner to an input of the intermediate processing device, and (c) redirect the input of the host to an output of the intermediate processing device. An entire new layer of ultrasound functionality (e.g., a special kind of real-time filtering or the like) has thus been added to the overall system, without requiring substantial costs in modifying or replacing existing system components.

Figure 2:
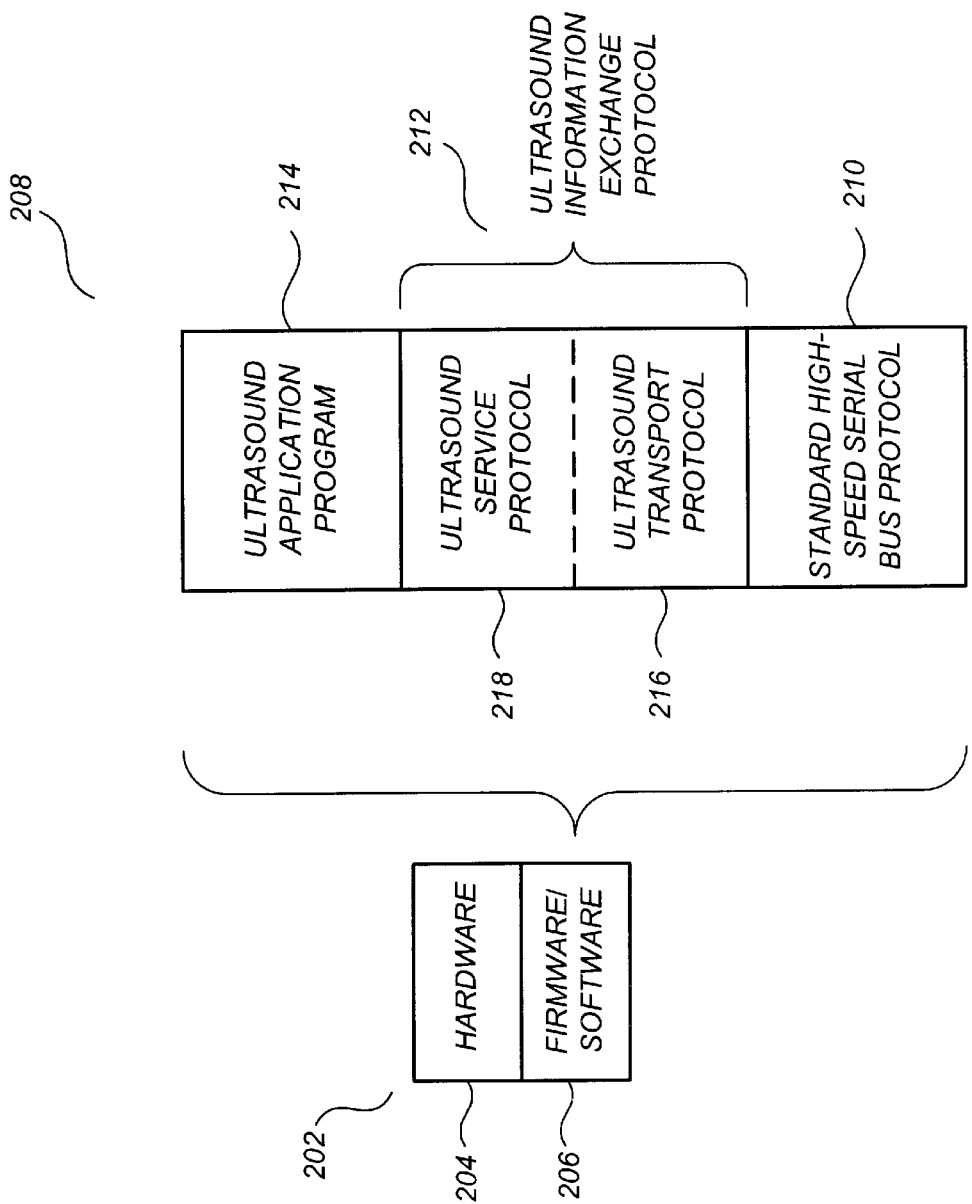
FIG. 2 shows an ultrasound information exchange protocol stack in accordance with a preferred embodiment.

FIG. 2 shows a block diagram of an exemplary ultrasound device 202 and a protocol stack 208 according to a preferred embodiment. The ultrasound device 202 comprises a hardware component 204 and a software component 206 for achieving any of the ultrasound functionalities described supra. The software component 206 comprises a lower protocol layer 210, an ultrasound information exchange protocol layer (UIEP) 212, and an ultrasound application layer 214.

The lower protocol layer 210 is adapted to implement communications between ultrasound devices in accordance with one of the high-speed serial bus protocols (e.g., IEEE 1394/1995, USB, Fibre Channel, etc.) described supra. The lower protocol layer 210 is preferably implemented using off-the-shelf application programming interfaces (APIs) known in the art. By way of non-limiting example, for a situation in which the ultrasound device 202 is based on the Microsoft Windows NT® platform and an IEEE 1394 serial bus is used for ultrasound information bus 102, the lower protocol layer program may comprise Microsoft's FireWire API for Windows NT®.

The ultrasound application layer 214 represents the implementation of any ultrasound application program (e.g., host programs, DSP programs, scanner programs, storage programs, etc.) as appropriate for the ultrasound device in question. More generally, ultrasound application layer 214 corresponds to any program associated directly or indirectly with devices that detect, process, store, analyze, display, or perform any other activity associated with ultrasound information.

In accordance with a preferred embodiment, the UIEP 212 lies between the lower protocol layer 210 and the application layer 214. The UIEP 212 is a lightweight protocol that provides a standard communications interface between any two ultrasound applications communicating across any high-speed packetized serial bus capable of supporting asynchronous and isochronous data transfer. In addition to being a standardized protocol for enabling ultrasound device interoperability, the UIEP is specially adapted for efficient transport and processing of ultrasound information by its respective source and destination devices and algorithms. As indicated in FIG. 2, UIEP 212 comprises an Ultrasound Transport Protocol (UTP) layer 216 and an Ultrasound Service Protocol (USP) layer 218.

Ultrasound Transport Protocol (UTP) layer 216 is adapted to provide a reliable, connection-oriented data delivery service between ultrasound ports of different ultrasound applications. The UTP layer establishes connection-oriented sessions over which data is reliably transmitted during the period that the session is open. The UTP layer establishes connections, negotiates session parameters, manages the transfer of data, and terminates the connection between ultrasound ports. A UTP layer program running on ultrasound device 202 comprises a set of application program interface routines (APIs) that are accessible by the application layer or the USP layer. A set of exemplary UTP APIs are included infra in a section entitled "Sample Ultrasound Transport Protocol Layer APIs." Using UTP API routines, an ultrasound application layer program may instantiate a virtual connection between predetermined ports of respective ultrasound devices that are created and managed at the UTP layer level. The predetermined ports may be either bidirectional or unidirectional. In accordance with the UIEP protocol, the set of predefined ports includes, by way of example and not by way of limitation: an image data port for receiving or transmitting bulk ultrasound image data; a hardware status port for providing a hardware status; a command/control port for receiving commands or control parameters from another ultrasound application; and other ports that may be defined in accordance with the UIEP as other needs may arise.

Table 1 shows an exemplary set of UTP ports according to a preferred embodiment. Table 2 shows an exemplary set of port status indicators that may be returned from a UTP API. As will be described infra with respect to the UTP packet structure, 8 bits are reserved for the ultrasound port ID in each UTP segment, and therefore up to 256 UTP ports may be defined.

TABLE 1

Ultrasound Transport Layer Ports

| PORT NUMBER | PORT NAME | DESCRIPTION |
| --- | --- | --- |
| 0 | UTP_RESERVED_PORT | Reserved for UTP communication |
| 1 | UTP_RESET_PORT | Reset device |
| 2 | UTP_RESET_ACK_PORT | Reset acknowledgment |
| 3 | UTP_COMMAND_PORT | Send or receive commands |
| 4 | UTP_ACK_PORT | Send or receive acknowledgements |
| 5 | UTP_STATUS_PORT | Request or receive status |
| 6 | UTP_BULK_DATA_PORT | Send or receive bulk data |
| 7–255 | RESERVED | |

TABLE 2

Ultrasound Transport Layer Port Status Indicators

| PORT STATUS | DEFINITION |
| --- | --- |
| UTP_OK | Operation completed successfully |
| UTP_INVALID_PARAMETER | One or more parameters is invalid |
| UTP_INIT_TIMEOUT | Initialization attempt timed out |
| UTP_ALREADY_INITIALIZED | Initialization attempted more than once |
| UTP_LINK_FAILURE | Link failure detected during operation |
| UTP_INSUFFICIENT_MEMORY | Not enough memory for the operation |
| UTP_UNKNOWN_PORT_ID | Port ID specified is not a UTP_PORT |
| UTP_INVALID_HANDLE | Handle specified was not for an open port |
| UTP_PORT_NOT_OPEN | Port had not yet been opened on the other end |
| UTP_PORT_ALREADY_OPEN | Port already opened for the same direction |
| UTP_INVALID_REQUEST | Wrong port type for requested operation |
| UTP_PORT_BUSY | Attempt to send when previous send still active |
| UTP_NO_BUFFER | No BULK DATA buffer has been allocated |

TABLE 2-continued

Ultrasound Transport Layer Port Status Indicators

| PORT STATUS | DEFINITION |
| --- | --- |
| UTP_BUFFER_TOO_SMALL | BULK DATA buffer too small for data received |
| UTP_BUFFER_OVERRUN | Some un-received BULK DATA in buffer overwritten |

Ultrasound Service Protocol (USP) layer 218 is adapted to provide an interface between the ultrasound application layer 214 and the UTP layer 216, providing a set of routines that may be invoked in order to transfer ultrasound information between the application layers of any two ultrasound devices coupled to the ultrasound information bus. From ultrasound application programmer's perspective, i.e., from the perspective of an industry device or algorithm manufacturer, the USP defines a set of APIs that may be called by a source ultrasound application in communicating with a destination ultrasound application provided by the same or different manufacturer. The ultrasound information being communicated is passed through the source ultrasound port, across the UTP connection, to the destination ultrasound port at the other end of the UTP connection, and finally to the destination application. Responsive to the ultrasound information communicated, the source ultrasound application may expect the destination ultrasound application at the other end of the UTP connection to properly interpret, act upon, and/or respond to that ultrasound information.

In accordance with a preferred embodiment, two major types of USP messages are defined in the UIEP specification: a bulk image data type, and an asynchronous message type. The bulk image data type is specially formatted for transferring in an efficient format bulk ultrasound information such as B-mode data, Color Doppler data, M-mode data, Spectral Doppler data, ECG data, or some other ultrasound data type. The asynchronous message type is flexibly formatted for messages other than bulk image data types, such as scan identifications, commands, addresses and address offsets, statuses, timers, hardware identifiers, and the like. A set of exemplary USP APIs is included infra in a section entitled "Sample Ultrasound Service Protocol Layer APIs."

Figure 3:
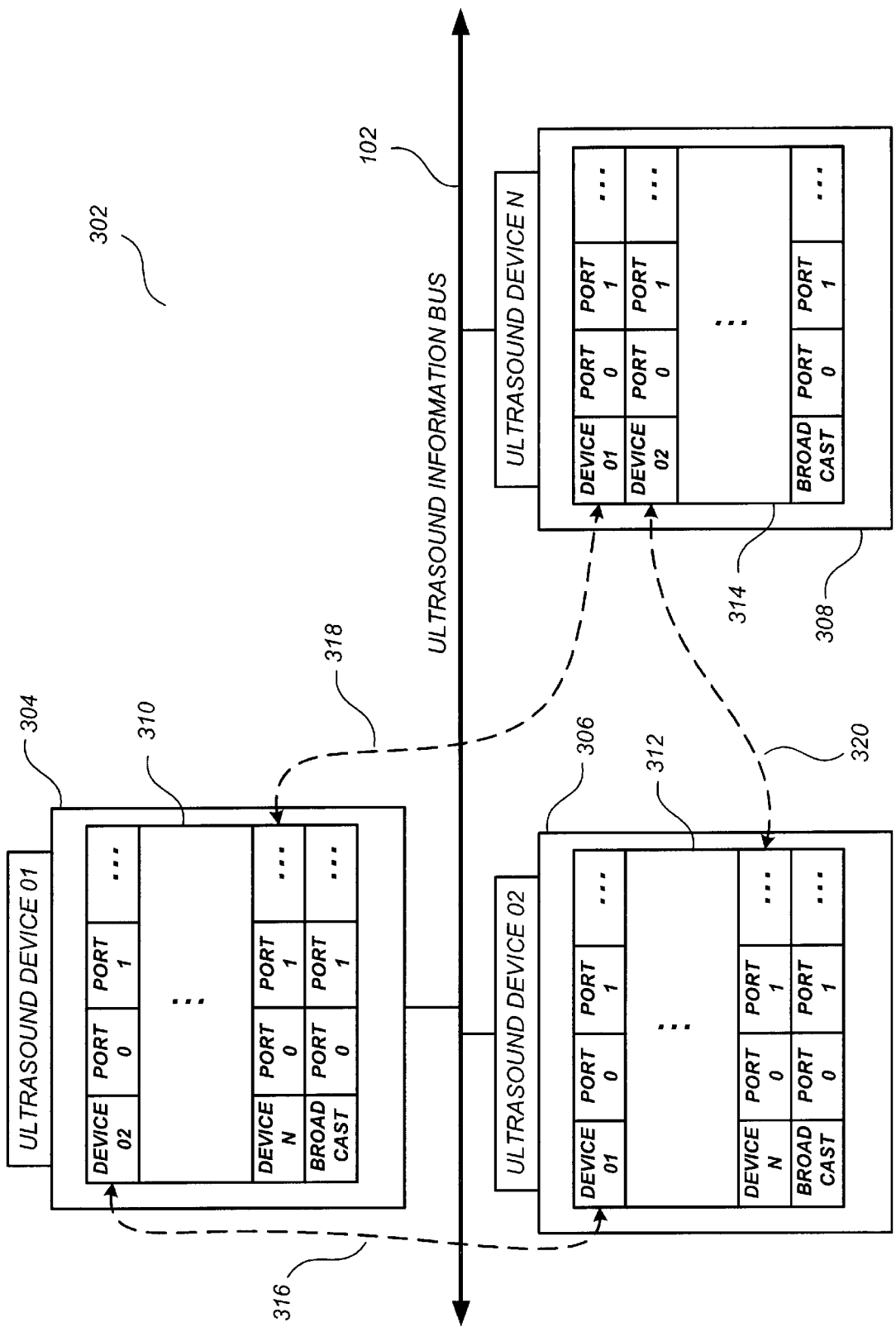
FIG. 3 shows a block diagram of ultrasound ports and connections for a plurality of ultrasound devices in accordance with a preferred embodiment.

FIG. 3 shows a block diagram of an ultrasound information processing system 302 with reference to the UTP ports and connections that may be defined therein. FIG. 3 shows a first ultrasound device 304 (for example, a host computer), a second ultrasound device 306 (for example, a scanning device), and a third ultrasound device 308 (for example, an intermediate ultrasound processor) each coupled to the ultrasound information bus 102. The ultrasound devices 304, 306, and 308 comprise UTP port tables 310, 312, and 314, respectively. According to a preferred embodiment, each UTP port table comprises, for each of the other ultrasound devices with which a connection-oriented communication session connection has been established, a complete set of the UTP port types that are indicated in Table 1, supra. The UTP port tables may be completely pre-established, or may be incrementally constructed as connection requests are made.

In the example of FIG. 3 in which the first ultrasound device 304 is a host computer and the second ultrasound device 306 is a scanning device, a dotted line 316 is drawn representing a virtual connection existing between the devices. With reference to Table 1, supra, the UTP layer establishes a connection oriented session between a first asynchronous command port of the host 304 (Row=Device 02, Column=Port 3=UTP_COMMAND_PORT) and a first asynchronous command port of the scanning device 306 (Row=Device 01, Column=Port 3=UTP_COMMAND_PORT). Asynchronous commands between the devices are transferred over the virtual connection represented by dotted line 316. In accordance with a preferred embodiment, the UTP layer programs send and receive these asynchronous commands over the asynchronous channel of the high-speed serial bus protocol being used at the physical/data link layer. This is done because the asynchronous commands generally do not require the "guaranteed on time" delivery services of the isochronous channel of the high-speed serial bus protocol, but do generally require the data integrity services of the asynchronous channel of the high-speed serial bus protocol.

In a configuration (not shown) in which only the host and scanning device are used in the system, there would be an additional virtual connection (not shown) between Port 6 (UTP_BULK_DATA_PORT) of the host and Port 6 (UTP_BULK_DATA_PORT) of the scanning device. Bulk ultrasound image data between the devices would be transferred over that virtual connection. In accordance with a preferred embodiment, the UTP layer programs would send and/or receive the bulk image data over the isochronous channel of the high-speed serial bus protocol being used at the physical/data link layer. This would be done because the bulk image data generally requires the "guaranteed on time" delivery services of the isochronous channel of the high-speed serial bus protocol in order to provide real-time ultrasound information processing capability.

In the more general case of FIG. 3 in which an intermediate processor 308 is included in the ultrasound information flow pipeline, bulk image data is gathered by the scanning device 306 and delivered to the intermediate processor 308 over a virtual connection 320 established between a bulk image port of the scanning device 306 (Row=Device N, Column=Port 6=UTP_BULK_DATA_PORT) and a first bulk image port of the intermediate processor 308 (Row=Device 02, Column=Port 6=UTP_BULK_DATA_PORT). Upon being processed by the intermediate processor 308, the bulk image data is delivered to the host 304 over a virtual connection 318 established between a second bulk image port of the intermediate processor 308 (Row=Device 01, Column=Port 6=UTP_BULK_DATA_PORT) and a bulk image data port of the host 304 (Row=Device N, Column=Port 6=UTP_BULK_DATA_PORT).

In the system of FIG. 3, process coordination commands from the host 304 to the scanning device 306 and/or the intermediate processor 308 are provided over virtual connections established between command ports of the devices. The command ports are selected from the UTP port tables 310, 312, and 314 as necessary (e.g., between the port at Row=Device N, Column=Port 3=UTP_COMMAND_PORT of host 304 and the port at Row=Device 01, Column=Port 3=UTP_COMMAND_PORT of intermediate processor 308). Alternatively, in accordance with another preferred embodiment, process coordination commands may be broadcast to UTP broadcast ports of the different devices, the UTP broadcast ports being shown as the last row in each of the UTP port tables 310, 312, and 314 of FIG. 3. When command delivery and response is completed, the virtual connections may be torn down, or may alternatively remain in anticipation of future command communications between the devices.

Figure 4:
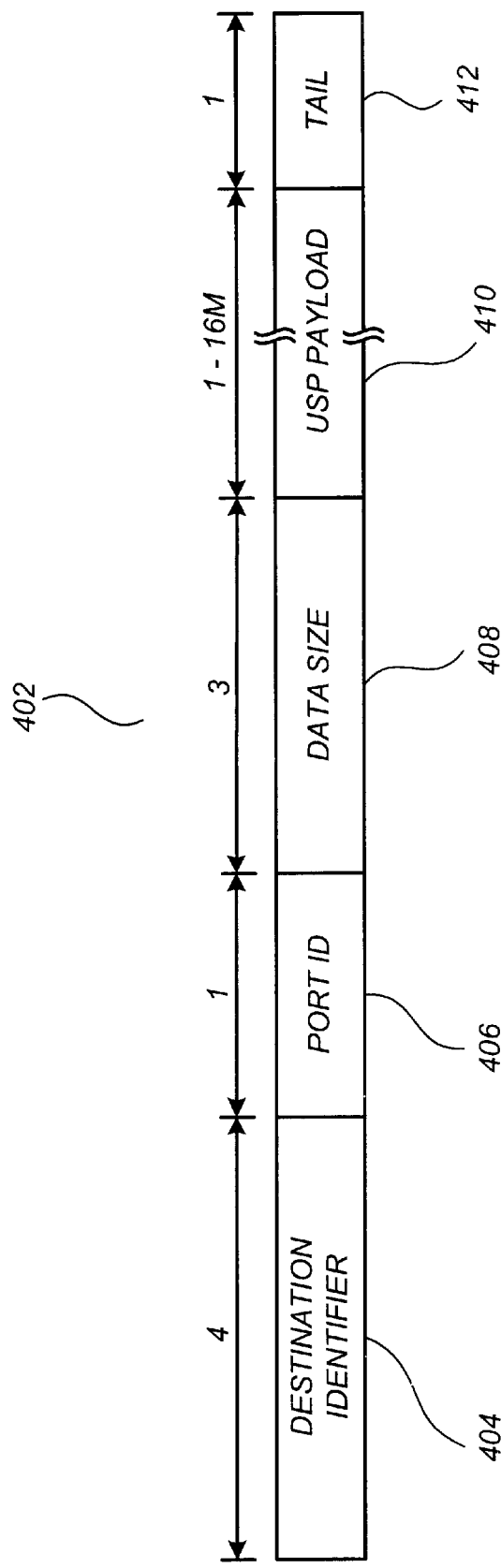
FIG. 4 shows an ultrasound transport protocol packet in accordance with a preferred embodiment.

FIG. 4 shows a diagram of a UTP packet 402 in accordance with a preferred embodiment. In accordance with the UIEP protocol, USP data frames are encapsulated within UTP packets for transfer between ultrasound devices, the USP frames representing a payload data portion within each UTP packet. UTP packet 402 comprises a 4-byte destination identifier 404, which in one preferred embodiment is a unique IP address. UTP packet 402 further comprises a 1-byte Port ID 406 for identifying the destination-port, a three byte data size field 408, a USP payload frame 410, and a 1 byte tail 412. The USP payload frame 410 may be anywhere in size from 1 to 16M bytes depending on the nature of the payload.

In accordance with a preferred embodiment, there is a predetermined mapping between port ID and the direction (send only, receive only, or bidirectional) of the data being transferred over that port. Furthermore, there is also a predetermined mapping between port ID and the high-speed serial bus protocol channel type (asynchronous or isochronous). For example, for an ultrasound host device, the port UTP_RESET_PORT is a send port, and the data is transferred over an asynchronous channel of the high-speed serial bus. As another example, for an ultrasound scanner, the port UTP_BULK_DATA_PORT is a send port, and the data is transferred over an isochronous channel of the high-speed serial bus. However, in an alternative preferred embodiment that is more generalized and does not require such predetermined mappings, the UTP packet 402 may also comprise a 1 byte port direction indicator (not shown) for identifying whether the port is in send, receive, or bidirectional mode. UTP packet 402 may also comprise a 1 byte data mode indicator (not shown) for identifying whether the port is associated with asynchronous or isochronous data transfer.

In accordance with a preferred embodiment, the UTP packet 402 represents the fundamental unit of data transfer at the UTP layer. However, depending on its size and on the nature of the standard high-speed serial bus protocol that is chosen, the UTP packet 402 may be broken up into smaller data units at the high-speed serial bus protocol layer for optimal transfer. Thus, for example, if the standard high-speed serial bus protocol has a maximum frame size of 1 Kbyte and the UTP packet 402 is greater than 1 Kbyte, it will be broken up accordingly before data transfer. Reassembly of the UTP packet data stream is handled at the high-speed serial bus protocol layer at the receiving end.

The payload being carried by the UTP packet 402, i.e., the USP payload frame 410, will have different internal structures depending on whether it carries asynchronous command data or isochronous bulk image data. Asynchronous command data generally includes any type of information that needs to be passed among ultrasound devices that is not bulk image data. By way of nonlimiting example, typical commands include open port, load code at logical address, run, status request, status request response, reset, reset acknowledge, stop, and close port. A more thorough yet nonlimiting set of exemplary commands is listed infra in the section entitled "Sample Ultrasound Transport Protocol Layer APIs."

In accordance with a preferred embodiment, the above "load code" command provided in the USP protocol is associated with loading code at a logical address in the destination ultrasound device. For example, where the destination device is a scanner and the source device is a remote host, the scanner has memory blocks that may be loaded and managed by the remote host. Advantageously, the remote host is not required to have knowledge of the specific memory architecture of the scanner. The UIEP of the preferred embodiments provides for communication and management of memory addresses in a logical address space, wherein physical memory addresses in the scanner are derived locally by adding the logical address offset to the corresponding hardware address.

Figure 5:
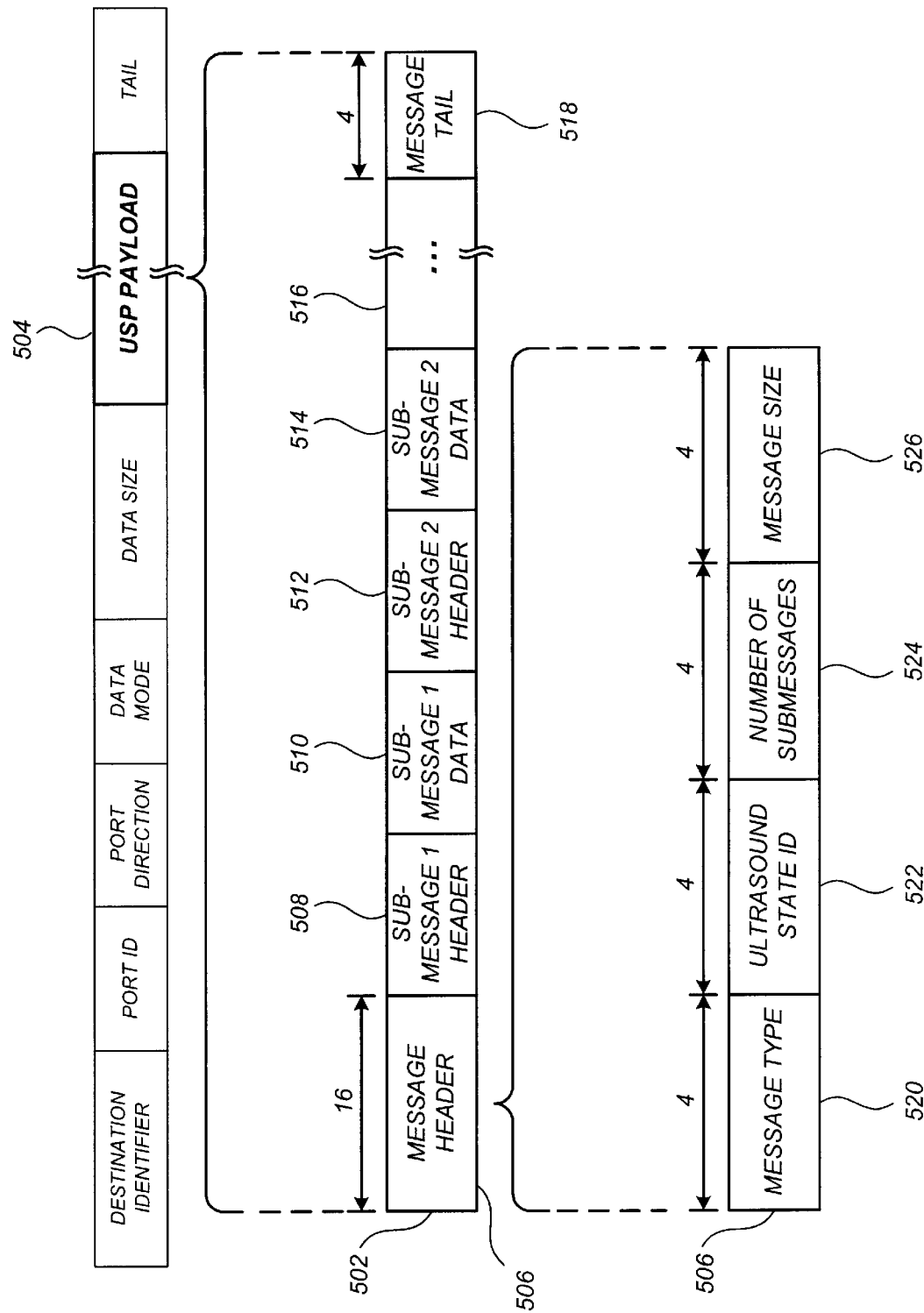
FIG. 5 shows an ultrasound service protocol frame carrying one or more asynchronous commands in accordance with a preferred embodiment.

FIG. 5 shows a USP frame 502 associated with an asynchronous command in accordance with a preferred embodiment. USP frame 502 is included within a USP payload field 504 of the UTP frame shown at the top of FIG. 5. USP frame 502 comprises a message header 506, and a plurality of submessages, each submessage having a header field and a data field. For example, USP frame 502 comprises a submessage 1 header 508, a submessage 1 data field 510, a submessage 2 header 512, a submessage 2 data field 514, and further submessages as represented by element 516, as well as a message tail 518. Message header 506 comprises a message type field 520, an ultrasound state ID field 522, a number-of-submessages field 524, and a message size field 526. These fields are described further in Table 3.

The USP frame 502 may comprise only a single submessage, or may comprise several submessages. Each submessage represents a distinct command, response, acknowledgment, etc., from the source device to the destination device. However, it has been found that several commands often need to be sent consecutively from one ultrasound device to another, and in such case it is convenient to group the commands into a single USP frame.

TABLE 3

Asynchronous Message Header

| FIELD NAME | SIZE | DESCRIPTION |
|---|---|---|
| Message Type | 4 bytes | Specifies source device type and destination device type for purposes of interpreting submessages. Examples include: host to scanner command; scanner to host status; scanner to host information; scanner acknowledgment. |
| Ultrasound State ID | 4 bytes | Indicates the ultrasound state to which this message refers. A change in this parameter indicates an alteration of one or more ultrasound scan parameters extrinsic to bulk data frame information, as described further infra. |
| Number of Sub-Messages | 4 bytes | Number of sub-messages included with this message. |
| Message Size | 4 bytes | Message size in bytes, including header. |

The submessage header included in asynchronous command frame 502 may vary in format depending on the nature of the source device, the nature of the destination device, the context of the communication, and the desired action or response. By way of nonlimiting example, Table 4 below shows a submessage header for the case where the sending device is a host and the receiving device is a scanner. Table 5 below shows a submessage header for the case where the sending device is a scanner and the receiving device is a host.

TABLE 4

Host to Scanner Submessage Header

| FIELD NAME | SIZE | DESCRIPTION |
|---|---|---|
| Submessage Type | 4 bytes | Examples include: Init (perform scanner initialization); Run (start scanning); Stop (stop scanning); Real-time program (change hardware parameters without stopping scan); Offline Program (program while no |

TABLE 4-continued

Host to Scanner Submessage Header

| FIELD NAME | SIZE | DESCRIPTION |
|---|---|---|
| Operation | 4 bytes | scanning); Request Probe Status; Request Scanner Hardware Status; Request Scanner Hardware Information; Request Scanner Software Information; Load DSP Code. Examples include: Load Hardware Data (load data into hardware RAM, registers, and DSP memory where addressing mode is specified by logical address); Set bits (set bits in location specified by logical address); Reset Bits (reset bits in location specified by logical address). |
| Logical Address | 4 bytes | Logical memory address in scanner from which Address Offset is referenced. Logical address is defined by host application software and translated into actual scanner hardware address by destination scanning device. |
| Address Offset | 4 bytes | Logical number that is combined with Logical Address to allow scanner software to access a portion of hardware memory. |
| Data Size | 4 bytes | Data size in bytes for submessage data section. |

TABLE 5

Scanner to Host Submessage Header

| FIELD NAME | SIZE | DESCRIPTION |
|---|---|---|
| Submessage Type | 4 bytes | Examples include: Probe Status Report (i.e., this submessage provides a probe status report); Scanner Hardware Status (reporting scanner hardware status); Scanner Hardware Information (e.g., reporting hardware RAM data, DSP software parameters, etc.); Scanner Software Status (reporting scanner software parameters). |
| Status ID | 4 bytes | ID for the reported status. |
| Logical Address | 4 bytes | Same as for Host to Scanner Submessage Header. |
| Address Offset | 4 bytes | Same as for Host to Scanner Submessage Header. |
| Data Size | 4 bytes | Data size in bytes for submessage data section. Set to zero if scanner to host submessage has no data section. |

The submessage data format also varies depending on the nature of the source device, the nature of the destination device, the context of the communication, and the desired action or response. By way of nonlimiting example, Table 6 below lists a scanner to host submessage data definition for a probe status report. Table 7 below lists a scanner to host submessage data definition for scanner hardware information. Table 8 below lists a scanner to host submessage data definition for a scanner software status request.

TABLE 6

Scanner to Host Submessage Data Definition: Probe Status Report

| FIELD NAME | SIZE | DESCRIPTION |
|---|---|---|
| Slot 1 Status | 4 bytes | Slot status indicating the state of the probe slot, e.g.: Disconnected; Connected but not Scanning; Connected and Scanning |
| Slot 1 Probe ID | 4 bytes | Unique ID of the Probe type that is connected to the slot. |
| Slot 2 Status | 4 bytes | (see above) |

TABLE 6-continued

Scanner to Host Submessage Data Definition: Probe Status Report

| FIELD NAME | SIZE | DESCRIPTION |
|---|---|---|
| Slot 2 Probe ID | 4 bytes | (see above) |
| Slot 3 Status | 4 bytes | (see above) |
| Slot 3 Probe ID | 4 bytes | (see above) |
| Slot 4 Status | 4 bytes | (see above) |
| Slot 4 Probe ID | 4 bytes | (see above) |

TABLE 7

Scanner to Host Submessage Data Definition: Scanner Hardware Information

| FIELD NAME | SIZE | DESCRIPTION |
|---|---|---|
| Hardware Raw Data | "N" Bytes | Contains the data in the scanner hardware or RAM specified by the logical address and offset contained in the Scanner to Host Submessage Header. Size "N" is specified in the Scanner to Host Submessage Header. |

TABLE 8

Scanner to Host Submessage Data Definition: Scanner Software Status

| FIELD NAME | SIZE | DESCRIPTION |
|---|---|---|
| High Voltage Status | 4 bytes | May include the following states: Normal; Overvoltage. |
| Watch Dog Timer | 4 bytes | May include the following states: Normal; Watch Dog timer triggered. |
| Other | 4 bytes | Other scanner software information |

Figure 6:
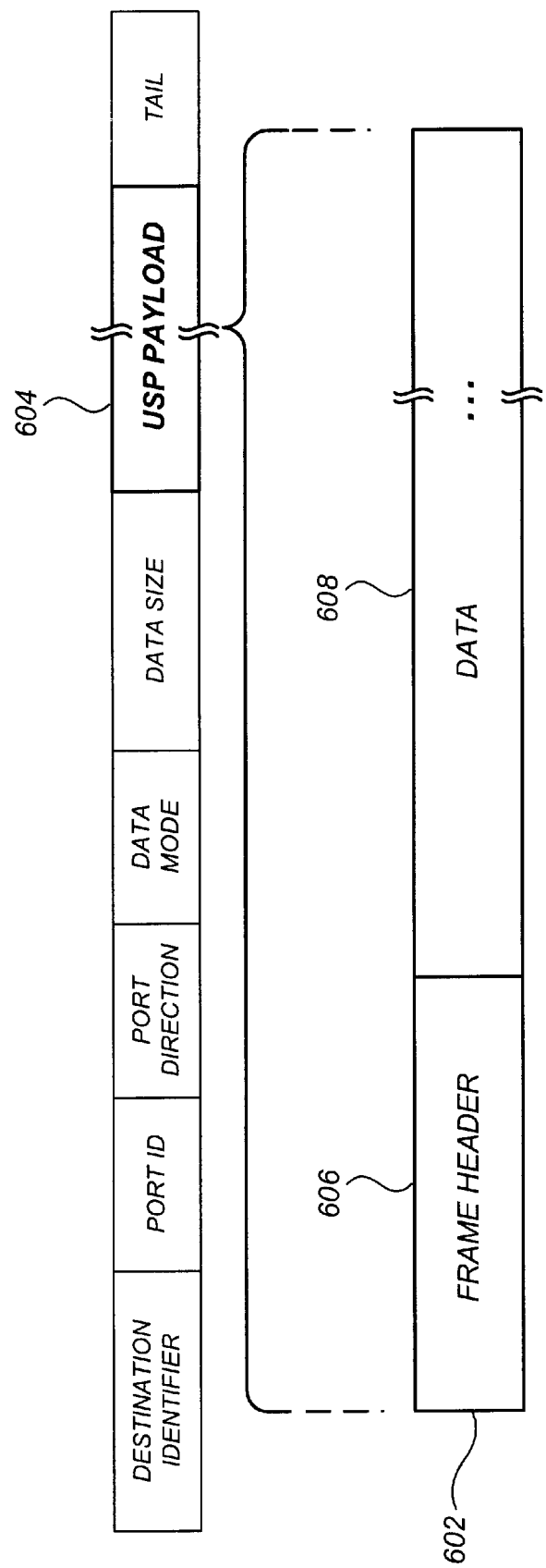
FIG. 6 shows an ultrasound service protocol frame carrying bulk ultrasound image data in accordance with a preferred embodiment.

FIG. 6 shows a USP frame 602 that is associated with a bulk image data frame in accordance with a preferred embodiment. USP frame 602 is included within a USP payload field 604 of the UTP frame shown at the top of FIG. 6. Bulk image USP frame 602 comprises a header field 606 and a data field 608. Generally speaking, each bulk image USP frame will include an entire frame of bulk ultrasound image data. Included within the scope of the preferred embodiments, however, is a case where a single USP payload comprises multiple ultrasound frames from different ultrasound modes, e.g., a M-mode header, M-mode data, B-mode header, and B-mode data. Also within the scope of the preferred embodiments is a case where a single USP frame includes multiple frames from the same ultrasound mode. Also within the scope of the preferred embodiments is a case where a single USP frame includes partial frames, with USP layer programs providing frame reconstruction services as necessary. The specific format of the header field 606 and data field 608 will vary, as described infra, depending on whether the data is B-mode data, Color Doppler data, M-mode data, Spectral Doppler data, ECG data, or other types of bulk ultrasound image data.

Figure 7:
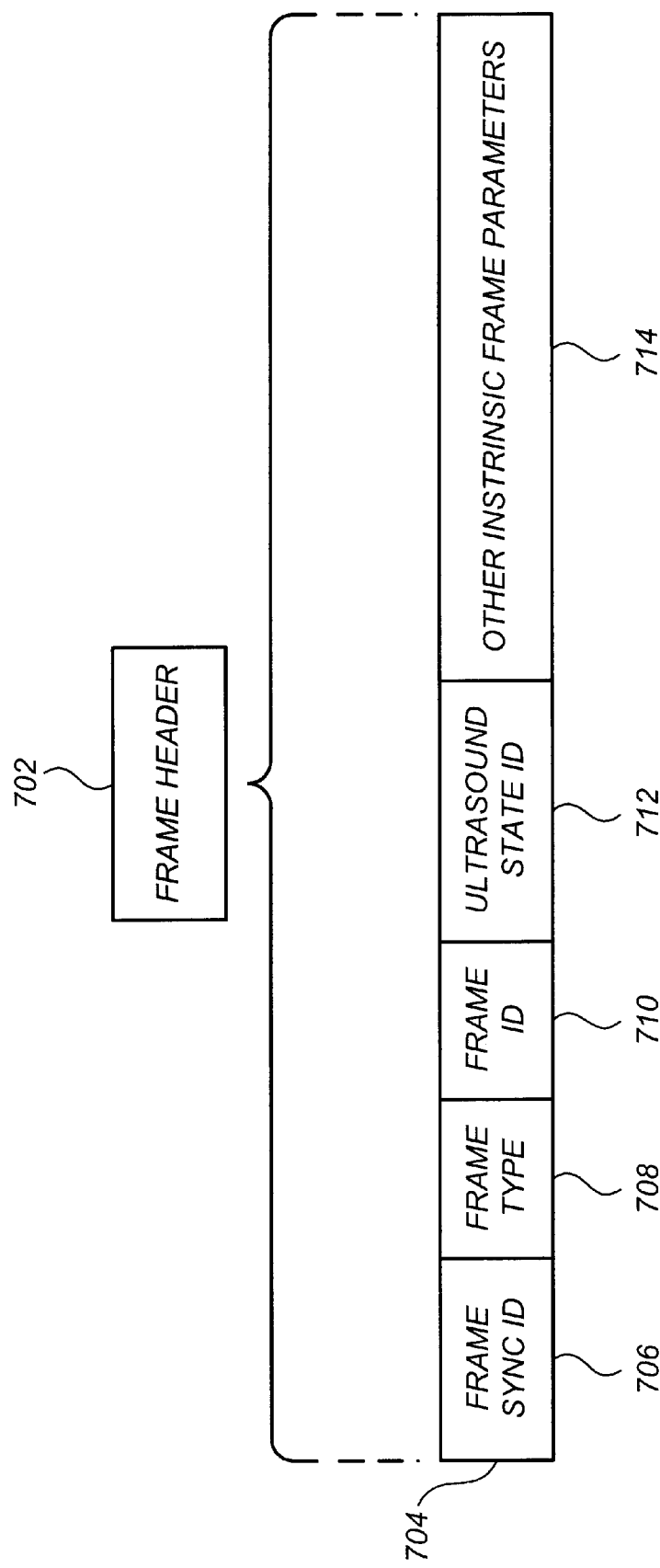
FIG. 7 shows a header of an ultrasound service protocol frame of FIG. 6.

FIG. 7 shows a diagram of a bulk image USP frame header 702 in accordance with a preferred embodiment, corresponding to the frame header 606 of FIG. 6. The frame header 702 comprises a frame sync ID field 706, a frame type field 708, a frame ID field 710, an ultrasound state ID field 712, and a field 714 for carrying other intrinsic frame parameters. In accordance with a preferred embodiment, an ultrasound source device, such as a scanner, generates image data in accordance with (a) intrinsic parameters that are included within each bulk data frame, together with (b)

extrinsic parameters that are not included within each bulk data frame. In the frame header of FIG. 7, for example, each of the fields 706, 708, 710, and 714 represent intrinsic parameters. However, for each bulk data frame, the host device requires knowledge of both the intrinsic and extrinsic parameters to properly process the frame. Examples of extrinsic parameters include, by way of nonlimiting example, pulse repetition frequencies and image magnification factors.

According to a preferred embodiment, the ultrasound state identifier 712 that is attached to each bulk image frame is an index, usually in a numerical format, used by the host device to locate the correct set of extrinsic parameters for processing that frame. In one embodiment, the ultrasound state ID may progress linearly as extrinsic parameters are changed, whereas in another embodiment, the ultrasound state ID may progress in a random fashion. It is of primary importance that, upon receiving the ultrasound state ID in a bulk image data frame, the host device (and any intermediate ultrasound device) is capable of obtaining the proper corresponding extrinsic parameters to use in processing that bulk image data. As will be described infra, sets of extrinsic parameters and their corresponding ultrasound state identifiers are communicated between the scanner and host (and any intermediate ultrasound device) using their asynchronous command ports or broadcast ports as the extrinsic parameters are varied. Synchronization, i.e. proper matching of the bulk data frames with the proper set of extrinsic parameters, is thereby preserved as the extrinsic parameters are varied.

Although the nature of the intrinsic frame parameters will vary depending on the ultrasound mode, these intrinsic frame parameters will usually include a frame sync ID, frame type, and frame ID. Accordingly, these have been shown as elements 706, 708, and 710 in FIG. 7, while all other intrinsic frame parameters are grouped as element 714. Tables 9–15 below provide further detail of examples of the header field and data field format used for B-mode (Tables 9–10), Color Doppler Mode (Tables 11–12), M-Mode (Table 13), Spectral Doppler (Table 14), and ECG mode (Table 15).

TABLE 9:

B-Mode Frame Header

| FIELD NAME | SIZE |
| --- | --- |
| Frame Sync ID | 4 bytes |
| Frame Type (B Mode) | 4 bytes |
| Frame Id | 4 bytes |
| Ultrasound State ID | 4 bytes |
| Starting Vector Number | 4 bytes |
| End Vector Number | 4 bytes |
| Start of ROI (multiple of 48 MHz) | 4 bytes |
| Number of Sample Volumes | 4 bytes |
| Number samples per vector (NSPV) | 4 bytes |
| X position in mm | 4 bytes |
| Y position in mm | 4 bytes |
| Z position in mm | 4 bytes |
| Rolling in degrees | 4 bytes |
| Yawing in degrees | 4 bytes |
| Pitching in degrees | 4 bytes |
| Packet size in bytes | 4 bytes |
| Reserved | to packet size |

TABLE 10

B-Mode Vector Data Definition

| FIELD NAME | SIZE |
| --- | --- |
| Vector line number | 4 bytes |
| B vector data samples | NSPV bytes |
| Reserved | to packet size |

TABLE 11

Color Doppler Frame Header

| FIELD NAME | SIZE |
| --- | --- |
| Frame Sync ID | 4 bytes |
| Frame Type (Color Doppler) | 4 bytes |
| Frame Id | 4 bytes |
| Ultrasound State ID | 4 bytes |
| Starting Vector Number | 4 bytes |
| End Vector Number | 4 bytes |
| Number samples per vector (NSPV) | 4 bytes |
| Packet size in bytes | 4 bytes |
| Reserved | to 512 bytes |

TABLE 12

Color Doppler Data Definition

| FIELD NAME | SIZE |
| --- | --- |
| Color Doppler sample 1 | 4 bytes, comprising: Velocity (1 byte); Variance (1 byte); Power (1 byte); and Reserved (1 byte) |
| Color Doppler sample 2 | 4 bytes, comprising: Velocity (1 byte); Variance (1 byte); Power (1 byte); and Reserved (1 byte) |
| . . . | 4 bytes, comprising: Velocity (1 byte); Variance (1 byte); Power (1 byte); and Reserved (1 byte) |
| Color Doppler sample 128 | 4 bytes, comprising: Velocity (1 byte); Variance (1 byte); Power (1 byte); and Reserved (1 byte) |

TABLE 13

M-Mode Header and Data

| FIELD NAME | SIZE |
| --- | --- |
| Frame Sync ID | 4 bytes |
| Frame Type (M) | 4 bytes |
| Frame Id | 4 bytes |
| Ultrasound State ID | 4 bytes |
| M Vector Number | 4 bytes |
| Start of ROI (multiple of 48 MHz) | 4 bytes |
| Number of Sample Volumes | 4 bytes |
| Number of samples per vector (NSPV) | 4 bytes |
| Packet size in bytes | 4 bytes |
| M samples | NSPV bytes |
| Reserved | to 1K bytes |

TABLE 14

Spectral Doppler Header and Data

| FIELD NAME | SIZE |
| --- | --- |
| Frame Sync ID | 4 bytes |
| Frame Type (Spectral Doppler) | 4 bytes |
| Frame Id | 4 bytes |
| Ultrasound State ID | 4 bytes |
| Doppler Vector Number | 4 bytes |
| Number samples per vector (NSPV) | 4 bytes |
| Packet size in bytes | 4 bytes |
| Spectral Doppler samples | Total of NSPV*4 bytes: I sample data (2 bytes) and Q sample data (2 bytes) per sample |
| Reserved | to 512 bytes |

TABLE 15

ECG Header and Data

| FIELD NAME | SIZE |
| --- | --- |
| Frame Sync ID | 4 bytes |
| Frame Type (ECG) | 4 Bytes |
| Frame Id | 4 bytes |
| Ultrasound State ID | 4 bytes |
| Number of samples (NS) | 4 bytes |
| Packet size in bytes | 4 bytes |
| ECG samples | NS bytes |
| Reserved | to 64 bytes |

Figure 8:
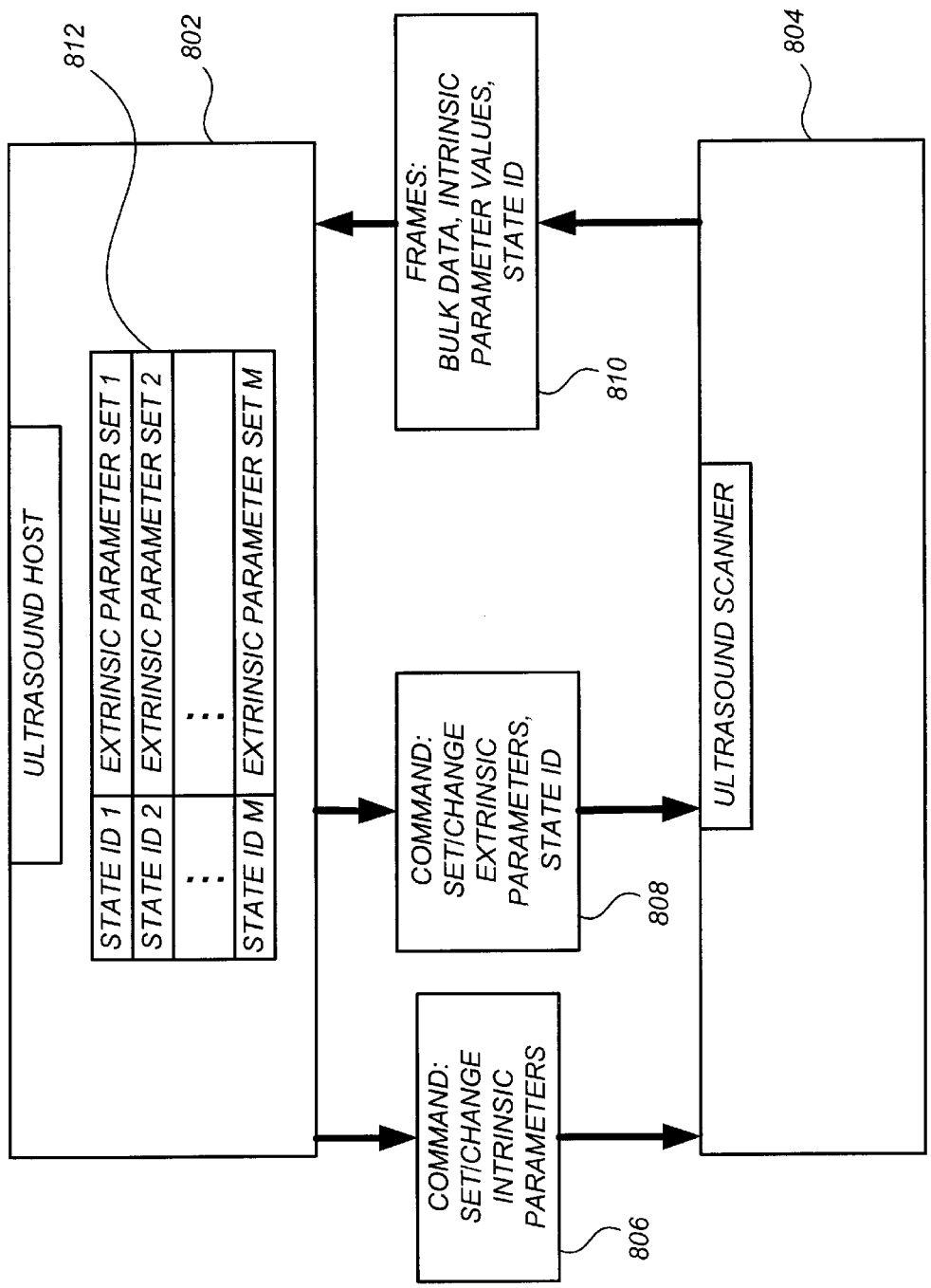
FIG. 8 shows a conceptual diagram of data flow that occurs during synchronization of two ultrasound devices in accordance with a preferred embodiment.

FIG. 8 shows a conceptual diagram of data flow that occurs during synchronization of two ultrasound devices in accordance with a preferred embodiment. For simplicity and clarity of disclosure, an exemplary configuration in which a host 802 is receiving bulk image data from a scanner 804 is described, it being understood that the methods disclosed herein may be extended to any set of ultrasound devices coupled to the ultrasound information bus 102. In the prior art parallel backplane architectures described supra in the background section, there is an inherently proper correlation between (i) the transfer of bulk image data, and (ii) the transfer of parameters that are needed to interpret the bulk image data. This is because the parameters are simply sent and received as needed across dedicated command/control busses that are provided in parallel to the busses carrying the bulk image data.

However, when serial bus communications are used between the scanner and the host, it represents a challenge to properly synchronize the parameters being transmitted on the asynchronous channels with the bulk image frames being transmitted on the isochronous channels. One possible solution, of course, is to append to each bulk image frame all possible parameters that may be needed to interpret the bulk image data. Although theoretically possible and within the scope of the preferred embodiments, such a solution would be less desirable. This is because (i) the amount of data being transferred across the isochronous channels would be unnecessarily large, (ii) a protocol for specifying the parameter formats would be unnecessarily complex, and (iii) such protocol would also require modification when new parameters (e.g. as associated with new ultrasound algorithms) are introduced into the art.

In accordance with a preferred embodiment, it has been found that synchronization is better achieved by classifying the above parameters into two classes: (a) intrinsic parameters that are included within each bulk data frame, and (b) extrinsic parameters that are not included within each bulk data frame. For any given bulk data frame, both sets of parameters are needed for proper processing. However, the extrinsic parameters are established and communicated "out of band" between the ultrasound devices using the asynchronous channels, thereby saving isochronous bandwidth and allowing increased simplicity and flexibility in the UIEP protocol. Because extrinsic parameters (such as image magnification) may vary dynamically, the ultrasound state ID is used to properly correlate each bulk image data frame to its respective set of extrinsic parameters.

Accordingly, in the conceptual diagram of FIG. 8, the ultrasound host 802 is shown asynchronously sending commands 806 that set or change intrinsic parameters in the scanner, as well as commands 808 that set or change extrinsic parameters in the scanner. Importantly, these parameter changes can occur before a scan starts or during an ongoing scan. In accordance with a preferred embodiment, whenever an extrinsic parameter (such as image magnification) is set or changed, a new ultrasound state ID is assigned to the new set of extrinsic parameters, and transmitted along with the command 808 that changes the extrinsic parameter.

The host 802 comprises an ultrasound state ID table 812 for keeping track of the specific extrinsic parameter settings that are associated with each ultrasound state ID. The scanner 804 may, but is not required to, maintain a corresponding list of ultrasound state ID's and extrinsic parameter settings. Rather, it is important only that, when generating a particular bulk image frame using a specific set of extrinsic parameters, the scanner attach the proper ultrasound state ID to the bulk image frame data 810 when sending it to the host 802. Of course, the scanner 804 also includes the corresponding set of intrinsic parameters with each bulk image frame. Upon receiving the bulk image frame 810, the host 802 performs a lookup into ultrasound state ID table 812 using the provided ultrasound state ID, finds the correct extrinsic parameters, and then uses these extrinsic parameters and the provided intrinsic parameters to process the bulk image data.

Figure 9:
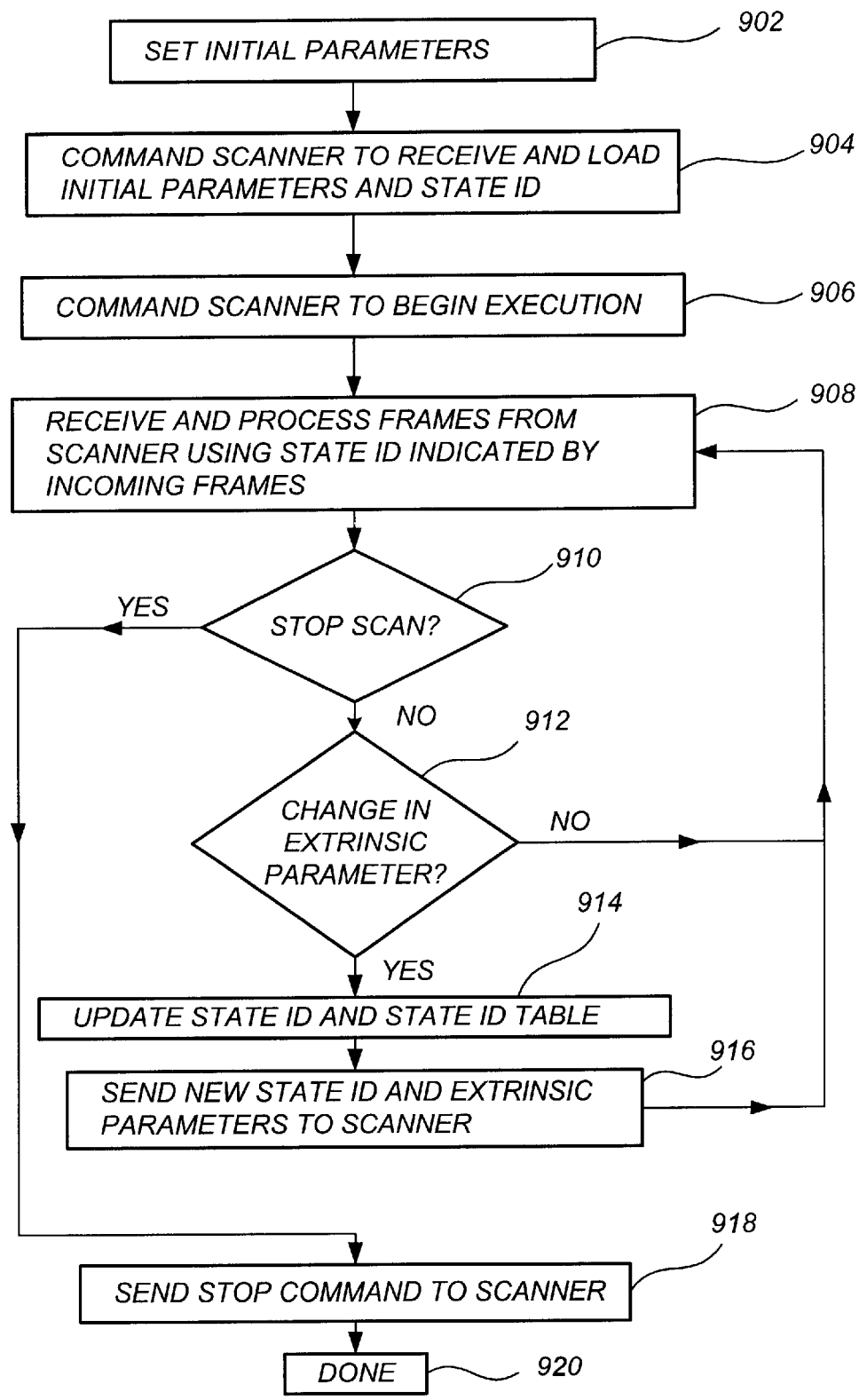
FIG. 9 shows steps taken during synchronization of two ultrasound devices in accordance with a preferred embodiment.

FIG. 9 shows steps taken during operation of the host device 802 of FIG. 8. At step 902, initial parameters (extrinsic and/or intrinsic) are set. At step 904, the host 802 commands the scanner 804 to receive and load the initial parameters and the ultrasound state ID associated with the extrinsic parameters. At step 906, the host 802 commands the scanner 804 to begin execution. At step 908, the host receives and processes frames from the scanner using the ultrasound state ID that is indicated by the incoming frames, as well intrinsic parameters being provided with each incoming frame. If the scan is complete at step 910, then a stop command is sent to the scanner at step 918 and the process is done at step 920. If the scan is not complete, operation continues at step 912. At step 912 it is determined whether there are any changes in the extrinsic parameters (such as image magnification). Such a change may occur, for example, responsive to user input changing the image magnification or other parameter. If there are no changes in extrinsic parameters, the algorithm continues at step 908.

However, if there is a change in the in extrinsic parameters, then at step 914 a new ultrasound state ID is chosen and loaded along with the new extrinsic parameters into the ultrasound state ID table 812. The numerical value of the ultrasound state ID may be incremented linearly, in a random fashion, or in any of a variety of manners, provided that it is different than a large number of its previous values. At step 916, the new extrinsic parameters and ultrasound state ID are sent to the scanner using the asynchronous command channel, and the process continues at step 908. At step 908, as each bulk image data frame arrives, the ultrasound state ID is compared to the ultrasound state ID table 812 for deriving the proper set of extrinsic parameters. Accordingly, after a recent extrinsic parameter change, even if there is "backup" of pipeline data associated with the old extrinsic parameters, the arriving frames are properly processed using the correct extrinsic parameters, and synchronization is maintained.

Figure 10:
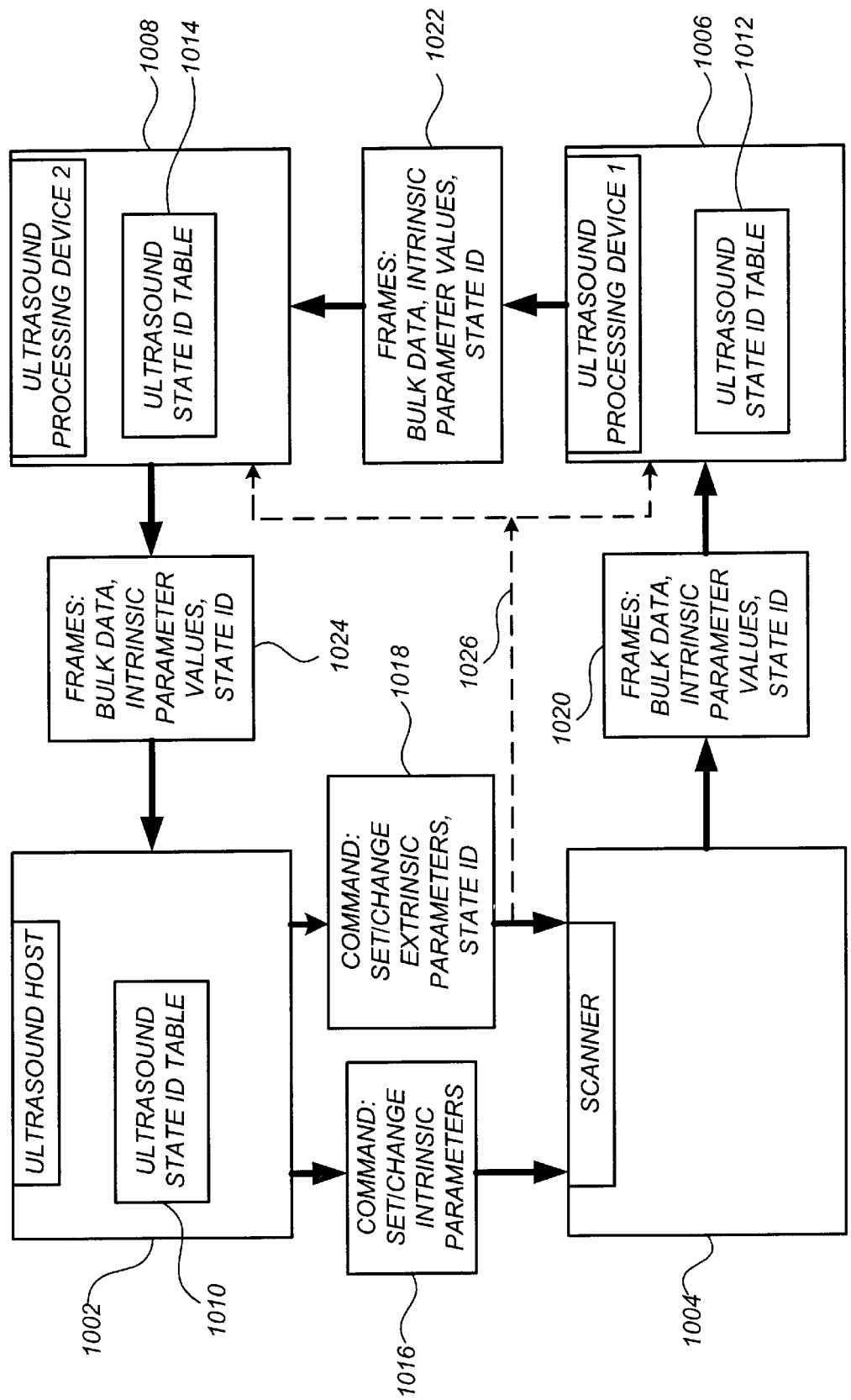
FIG. 10 shows a conceptual diagram of data flow that occurs during synchronization among four ultrasound devices in accordance with a preferred embodiment.

FIG. 10 shows a conceptual diagram of data flow that occurs during synchronization of more than two (in particular, four) ultrasound devices in accordance with a preferred embodiment. As described supra in the present disclosure, additional ultrasound processing devices may be attached to the ultrasound information bus, and inserted into the ultrasound data flow between the scanner and host. FIG. 10 shows an ultrasound host 1002, a scanner 1004, a first intermediate processing device 1006, and a second intermediate processing device 1008. As with the two-device configuration of FIG. 8, the host 1002 comprises in ultrasound state ID table 1010. Host 1002 sends asynchronous commands 1016 to the scanner 1004 for setting and changing intrinsic parameters, and sends asynchronous commands 1018 to the scanner 1004 for setting or changing extrinsic parameters. A new ultrasound state ID is sent with each change or setting of the extrinsic parameters. As shown in FIG. 10, each of the intermediate processing devices 1006 and 1008 also maintain their own ultrasound state ID tables 1012 and 1014, respectively, using information originating from host 1002.

As bulk data frames 1020 are generated by scanner 1004, they are now transmitted to the first intermediate device 1006. Upon processing each bulk data frame using (i) the provided intrinsic parameters, and (ii) the proper extrinsic parameters as derived from ultrasound state ID table 1012, intermediate device 1006 then proceeds to send the processed frames 1022 to the second intermediate device 1008. In turn, upon processing each incoming data frame using (i) the provided intrinsic parameters, and (ii) the proper extrinsic parameters as derived from ultrasound state ID table 1014, intermediate device 1008 then proceeds to send the processed frames 1024 to the host 1002, including the corresponding intrinsic parameter values and ultrasound state ID. Finally, the host 1002 processes the frames according to provided intrinsic parameters and the proper extrinsic parameters as derived from its ultrasound state ID table 1010.

In accordance with a preferred embodiment, host 1002 may transmit asynchronous commands that set or change the extrinsic parameters directly to the scanner 1004 only. The commands may then be forwarded in a serial fashion to the intermediate processing devices 1006 and 1008 for populating their ultrasound state ID tables. In accordance with another preferred embodiment, host 1002 may transmit the new extrinsic parameter information directly to each of the intermediate processing devices 1006 and 1008. In accordance with still another preferred embodiment, host 1002 may broadcast or multicast the new extrinsic parameter information to the intermediate processing devices 1006 and 1008. The direct transmission, multicast, or broadcast of the extrinsic parameters to the intermediate processing devices 1006 and 1008 is represented by the dotted line 1026 in FIG. 10.

Figure 11:
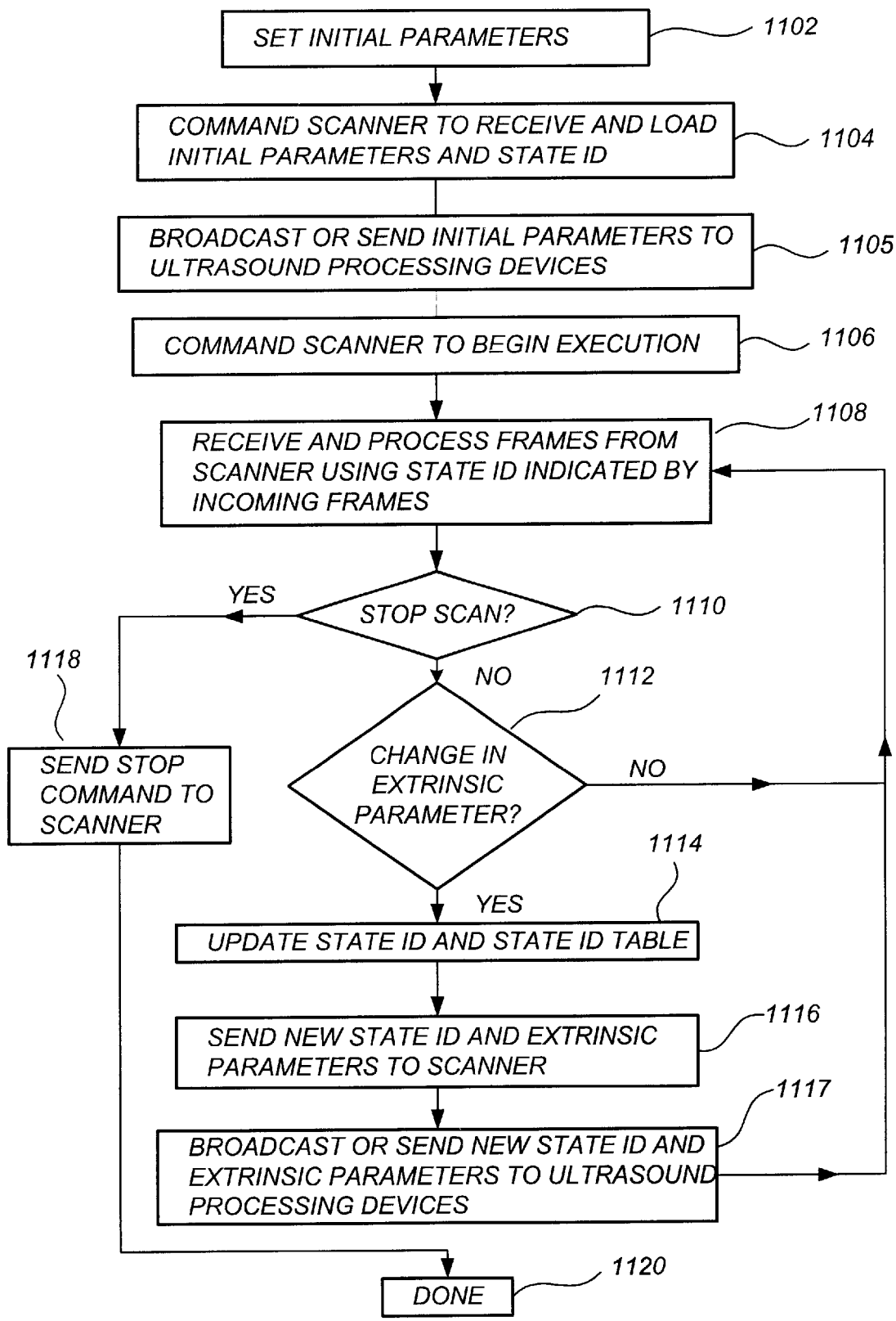
FIG. 11 shows steps taken during synchronization among four ultrasound devices in accordance with a preferred embodiment.

FIG. 11 shows steps corresponding to the operation of the host 1002 of FIG. 10. At step 1102, initial parameters are set. At step 1104, host 1002 commands the scanner to receive and load initial parameters and the beginning ultrasound state ID. At step 1105, host 1002 broadcasts, multicasts, or directly sends the initial extrinsic parameters and ultrasound state ID to the intermediate processing devices 1006 and 1008. The host 1002 may optionally pre-send the entire ultrasound state ID table 1010, or portions thereof, to the intermediate processing devices 1006 and 1008. As described supra, in lieu of the direct sending, multicast, or broadcast of the extrinsic parameter and ultrasound state ID information to the intermediate processing devices 1006 and 1008, this information may alternatively be stored-and-forwarded around the data path in a serial fashion.

At step 1106, host 1002 commands scanner 1004 to begin execution. At step 1108, host 1002 receives and processes frames using the ultrasound state ID that is indicated by the incoming frames, as well as the intrinsic parameters being provided within each incoming frame. Importantly, as this is happening, each of the intermediate processing devices 1006 and 1008 is doing the same thing, i.e., receiving incoming frames and accessing its respective ultrasound state ID table to determine the proper extrinsic parameters for processing those frames. Each of the intermediate devices 1006 and 1008 transmits the processed frames to the next device in the chain.

If the scan is complete at step 1110, then a stop command is sent to the scanner at step 1118 and the process is done at step 1120. If the scan is not complete, operation continues at step 1112. At step 1112 it is determined whether there are any changes in the extrinsic parameters (such as image magnification). If there are no changes in extrinsic parameters, the algorithm continues at step 1108. However, if there is a change in the in extrinsic parameters, then at step 1114 a new ultrasound state ID is chosen and loaded along with the new extrinsic parameters into the ultrasound state ID table 1010. At step 1116, the new extrinsic parameters and ultrasound state ID are sent to the scanner using the asynchronous command channel. At step 1117, the new ultrasound state ID and extrinsic parameters are directly sent, multicast, or broadcast to the intermediate processing devices 1006 and 1008 (or may alternatively be sent serially around the device chain). The process then continues at step 1108. In the above manner, synchronization is maintained because frames generated before a recent extrinsic parameter change will be properly matched with the correct "old" extrinsic parameters.

Sample Ultrasound Transport Protocol Layer APIs

The application program interfaces (APIs) for an exemplary implementation of the Ultrasound Transport Protocol Layer (UTP) are now described by way of nonlimiting example. For simplicity and clarity of disclosure, the APIs below presume a master-slave relationship between an ultrasound host node, such as an overall system control and user display unit, and an ultrasound slave or embedded device, such as an ultrasound scanner. Additionally, each UTP port in the APIs below is presumed to be one-way as opposed to bidirectional. However, based on the present disclosure, one skilled in the art could readily implement APIs for implementing the more general Ultrasound Transport Protocol Layer functionality disclosed supra in the present disclosure. Although the data types and API calls described below are based on the C/C++ programming language, they are readily adaptable to any object-oriented programming language or platform that enables multi-threaded execution flow. Data types such as UTP_STATUS, UOS_STRING, UTP_PORT_HANDLE and the like may be defined as appropriate for holding the requisite amounts of data required for the function indicated by that data type name.

UTP_STATUS UTP_Init (UTP_LINK_MODE ulmAppMode);

This API initializes UTP layer communication between two ultrasound devices. The argument ulmAppMode identifies whether the calling application will represent the master or the slave in this UTP layer connection. The calling application must call this initialization routine to configure the UTP layer as either in master or slave mode before making any other API call. An application on only one ultrasound device should initialize the UTP layer as a master. If more than one does so, operation of the UTP layer is undefined. A second attempt to initialize the UTP layer on the same processor will not re-initialize it but will return a status of UTP_ALREADY_INITIALIZED. When this API is called, the UTP layer, after performing the initialization step, will wait until communication is established with the other UTP layer before completing the operation. If the communication is not established within a system configurable amount of time, this operation will fail. This function returns UTP_OK if the function succeeds, otherwise it returns a UTP_STATUS value indicating the cause of failure: UTP_OK; UTP_INVALID_PARAMETER; UTP_INIT_TIMEOUT; UTP_ALREADY_INITIALIZED; or UTP_INSUFFICIENT_MEMORY.

UTP_STATUS UTP_Term (void);

This API will terminate the operation of the UTP connection. The UTP layer will close all open ports, discard any pending message, disable the communication link, and free up all resources that it has allocated. This function always returns UTP_OK.

UOS_STRING UTP_ErrorString (UTP_STATUS uStat);

This API may be invoked upon receiving an error message from an ultrasound device, and requests a string value that describes the specified error status. The specified error status is sent via the argument uStat. The returned UOS_STRING value is of a format that may be operating system dependent. In the case of Windows NT, for example, this will be std::string, and in the case of an embedded RTOS could be char*. If the specified uStat is not a valid UTP_STATUS, a string similar to "UTP Unknown Status" will be returned.

UTP_STATUS UTP_OpenPort (UTP_PORT upPortID, UTP_PORT_MODE upmMode, UTP_PORT_HANDLE *puphPort);

This API establishes a one-way communication mechanism between an application running on the master and the slave processor. An application is required to call this API to obtain a port handle to be used in subsequent calls to UTP_ClosePort( ), UTP_AllocateBulkDataBuffer( ), UTP_FreeBuffer( ), UTP_Send( ), or UTP_Receive( ). In order for communication to occur through a port, the port must be open for SEND on either the master or the slave and for RECEIVE on the other. This call blocks until the port is opened on the other side for the alternate direction. If the port has already been opened for the same direction by some other application, this call will fail with a status of UTP_PORT_ALREADY_OPEN. The argument upPortID is the ID of the requested port (e.g. UTP_HOST_CONTROL_PORT, UTP_EMBEDDED_STATUS_PORT). The argument upmMode is the mode (i.e., SEND or RECEIVE, MESSAGES or BULK_DATA) that this port is being opened for. The argument puphPort is the address of a UTP_PORT_HANDLE into which the assigned port handle will be stored. This API returns a UTP_STATUS value indicating the status of the operation, which may be one of the following: UTP_OK; UTP_INVALID_PARAMETER (upmMode is bad or puphPort is NULL); UTP_LINK_FAILURE; UTP_INSUFFICIENT_MEMORY; UTP_UNKNOWN_PORT_ID; or UTP_PORT_ALREADY_OPEN.

UTP_STATUS UTP_ClosePort (UTP_PORT_HANDLE uphPort);

This API closes the port specified by the handle returned from a previous call to UTP_OpenPort( ). All system resources allocated by the UTP layer for this port will be released. If this port is opened for RECEIVE, all messages or bulk data destined for this port will be discarded. If this port is opened for SEND, all messages that have been sent through this port will be delivered, if possible, prior to the completion of this API (the call will block until this condition is met). After this call is made, the handle is no longer valid. If desired to communicate through the port after it is closed, it must be re-opened by calling UTP_OpenPort( ) again. It is possible for one application to close a port on one end, and the communicating port to leave it open on the other. If a sending application closes a port, the receiving end will act normally as though there are no messages pending for it (after it has received all the messages sent prior to the sender closing the port). If a receiving application closes a port, all send attempts to send through the port by the sending application will fail with a status of UTP_PORT_NOT_OPEN. This API returns a UTP_STATUS value indicating the status of the operation, which may be one of the following: UTP_OK, or UTP_INVALID_HANDLE.

UTP_STATUS UTP_AllocateBulkDataBuffer (UTP_PORT_HANDLE uphPort, int nBufferSizeInBytes);

This API is called by the application to set up a buffer in which to receive bulk data. All bulk data received through that port will be placed into that buffer in a circular manner, i.e., it will wrap around to the beginning of the buffer if it is determined that the bulk data currently being sent will not fit contiguously at the end of the buffer. The argument uphPort is the handle of the port returned from UTP_OpenPort( ). The argument nBufferSizeInBytes is the number of bytes this buffer will be able to hold. This API returns a UTP_STATUS value indicating the status of the operation, which may be one of the following: UTP_OK; UTP_INSUFFICIENT_MEMORY; UTP_INVALID_HANDLE; or UTP_INVALID_REQUEST (port is not open for UTP_BULK_DATA_RECEIVE).

UTP_STATUS UTP_FreeBuxffer (UTP_PORT_HANDLE uphPort);

This API frees the receive data buffer allocated to the port that is specified by the argument uphPort. This buffer could have been either a bulk data receive buffer as allocated by UTP_AllocateBulkDataBuffer( ) or could be the message buffer automatically allocated by the UTP layer in the most recent call to UTP_Receive( ). Note that message receive buffers allocated by the UTP layer and returned in UTP_Receive will automatically be freed upon the subsequent call to UTP_Receive. This API returns a UTP_STATUS value indicating the status of the operation, which may be one of the following: UTP_OK; or UTP_INVALID_HANDLE.

UTP_STATUS UTP_SetReceiveNotify (UTP_PORT HANDLE uphPort, UOS_THREAD QUEUE uqhQueue, UOS_MSG_TYPE umtMsgType);

This API provides the UTP layer with a message queue specified by the argument uqhQueue into which notification messages will be posted indicating that a message or some bulk data has been received on the port specified by the argument uphPort. The argument uqhQueue is the UOS thread queue to which messages received on this port will be placed. The argument umtMsgType is the UOS message type that messages posted to that queue will have. The posted message will be of the message type specified by umtMsgType and contain as a message parameter the UTP_PORT_HANDLE of the port through which that message or bulk data was received. For each message already pending at this port when UTP_SetReceiveNotify( ) is called, a message will be posted to the specified queue as a result of the call. If UTP_SetReceiveNotify( ) had already been called prior to this call, the values of uqhQueue and umtMsgType will override the ones previously set. Specifying uqhQueue as UOS_NULL_QUEUE will disable receive notification on this port. This API returns a UTP_STATUS value indicating the status of the operation, which may be one of the following: UTP_OK; UTP_INVALID_PARAMETER (uqhQueue is not a valid UOS_THREAD_QUEUE); UTP_INSUFFICIENT_MEMORY; UTP_INVALID_HANDLE; or UTP_INVALID_REQUEST (port is not open for RECEIVE).

UTP_STATUS UTP_Send (UTP_PORT_HANDLE uphPort, PUTP_BUFFER_DESC *ppubdBufferDesc, int nDesc);

This API sends a message or a set of bulk data blocks through the port specified by the argument uphPort. The argument ppubdBufferDesc points to an array of pointers to UTP_BUFFER_DESCs, and the length of that array (in number of such pointers) is specified by the argument nDesc. The message or set of bulk data blocks will be sent in the order specified, and will be received into a contiguous buffer on the receiving end. When all data sent has been placed into that receive buffer, the UTP layer on the receiving end will either post a notification to the queue associated with that port or complete a UTP_Receive( ) operation, whichever is appropriate. This API is a blocking call and will complete when the data is fully contained in the receive buffer (it does not need to be received by the receiving application). The sending application may then call UTP_Send( ) again. If the application on the receiving end does not immediately receive the buffer, it will be held until received by the receiving application, and no messages will be lost. This API returns a UTP_STATUS value indicating the status of the operation, which may be one of the following: UTP_OK; UTP_INVALID_PARAMETER (ppubdBufferDesc is NULL or nDesc is zero); UTP_LINK_FAILURE (link failure detected during send attempt); UTP_INSUFFICIENT_MEMORY (not enough memory for receive buffer); UTP_INVALID_HANDLE; UTP_INVALID_REQUEST (port is not open for SEND); or UTP_PORT_BUSY.

UTP_STATUS UTP_Receive (UTP_PORT_HANDLE uphPort, PUTP_BUFFER_DESC pubdBufferDesc, int *pnReceivesPending);

This API will, if the port specified in the argument uphPort was opened in UTP_MESSAGE_RECEIVE mode, free the UTP layer allocated buffer referred to in the UTP_BUFFER_DESC that was returned in the previous call to this APT, and that buffer may no longer be used. The argument pubdBufferDesc is the port data descriptor as explained supra. The argument pnReceivesPending is a pointer to memory location that is to receive the number of sends still pending in the receive queue for this port after this one is removed. This API then fills in the UTP_BUFFER_DESC specified by pubdBufferDesc with the pointer to and the size, in bytes, of the oldest data buffer (either bulk data or message data) that arrived on the specified port and returns the status of the data received in that buffer. This API will indicate the number of buffers remaining after the one received by storing that information in the location specified by pnReceivesPending. If this value is NULL, that information will not be provided. If the port was opened in UTP_BULK_DATA_RECEIVE mode and either the amount of data sent is larger than the allocated buffer or the buffer had filled up and the oldest buffer segment not yet returned in a call to UTP_Receive had been overwritten, the UTP_BUFFER_DESC will still indicate the correct bufSize that had been transferred. In the former case the buffer contents will not be overwritten, pBuf will be invalid, and a UTP_STATUS of UTP_BUFFER TOO_SMALL will be returned. In the latter case, the oldest buffer segments will be overwritten, the pBuf value will point at overwritten data and a UTP_STATUS of UTP_BUFFER_OVERRUN will be returned. Note that, in the case of UTP_BUFFER_OVERRUN and possibly in the case where no un-received buffer segments at all were overwritten, the buffer segment returned in the most recent call to UTP_Receive( ) may be overwritten while being processed by the client. In order to avoid this potentially hazardous condition, it is recommended that the client monitor the status of the buffer using the information provided through pnReceivesPending to receive and discard all buffer segments that could possibly fall into this category shortly thereafter. If the port is open in UTP_BULK_DATA_RECEIVE mode and the UTP layer has detected an integrity failure in the data transferred, a status of UTP_INTEGRITY_FAILURE will be returned.

This API is a blocking call, waiting till a message or bulk data buffer has been received. If used in conjunction with UTP_SetReceiveNotify( ), this call will not block, since a buffer will always be available if such notification has been made. UTP_Receive( ) will also unblock if the port is closed and will return a status of UTP_PORT_NOT_OPEN. This API returns a UTP_STATUS value indicating the status of the operation, which may be one of the following: UTP_OK; UTP_INVALID_PARAMETER (pubdBufferDesc is NULL); UTP_LINK_FAILURE (link failure detected during receive attempt); UTP_INSUFFICIENT_MEMORY (not enough memory for receive buffer); UTP_PORT_NOT_OPEN (port was closed while receive pending); UTP_INVALID_REQUEST (port is not open for RECEIVE); UTP_BUFFER_OVERRUN (some bulk data overwritten, this not the oldest); UTP_INVALID_HANDLE; UTP_BUFFER_TOO_SMALL; or UTP_INTEGRITY_FAILURE;.

Sample Ultrasound Service Protocol Layer APIs

The application program interfaces (APIs) for an exemplary implementation of the Ultrasound Service Protocol Layer (USP) are described herein by way of nonlimiting example. For simplicity and clarity of disclosure, the APIs below presume a simple case of an ultrasound host, such as an overall system control and user display unit, and an ultrasound scanner. However, based on the present disclosure, one skilled in the art could readily implement APIs for implementing the more general Ultrasound Service Protocol Layer functionality disclosed supra in the present disclosure. Although the data types and API calls described below are based on the C/C++ programming language, they are readily adaptable to any object-oriented programming language or platform that enables multi-threaded execution flow. Table 16 shows USP layer data definitions associated with the USP API's described herein.

TABLE 16

Ultrasound Service Protocol Layer Data Definitions

```
typedef enum {
    kMsgCommand,            /* host to scanner command
                               message */
    kMsgAcknowledge,        /* acknowledge message */
    kMsgStatus              /* scanner to host status message */
} USP_MESSAGE_TYPE;
typedef enum {
    kSMsgInit,              /* Scanner initialization */
    kSMsgStop,              /* Stop the scanner */
    kSMsgRun,               /* Starting run the scanner */
    kSMsgRealTimeProgram,   /* program scanner HW without
                               stop it */
    kSMsgOfflineProgram,    /* program scanner while scanner
                               stopped */
    kSMsgLoadInputComp,     /* load input compression curve */
    kSMsgLoadDspCode        /* load dsp binary code */
    kSMsgReqProbeStatus,    /* request probe connection
                               status */
    kSMsgReqestHWStatus,    /* request scanner HW status */
    kSMsgReqestSWStatus,    /* request scanner SW status */
    kSMsgReqestHWInfo,      /* request scanner HW
                               information */
    kSMsgReportProbeStatus, /* report probe status */
    kSMsgReportHWStatus,    /* report scanner HW status */
    kSMsgReportSWStatus,    /* report scanner SW status */
    kSMsgReportHWInfo       /* report HW information */
} SUB_MESSAGE_TYPE;
typedef enum {
    kOpLoadHW,
    kOpReadHW,
    kOpSetBits,
    kOpResetBits
} SUB_MESSAGE_OPERATION;
typedef struct tagAsyncMsgHeader {
    UI32 uiMsgHeader;       /* unique Id for asynchronous
                               message */
    UI32 ultrasoundStateID; /* unique Id for ultrasound state */
    UI32 uiMsgType;         /* message type */
    UI32 uiNumOfSubMsg;     /* number of sub messages */
    UI32 uiDataSizeBytes;   /* message header size in bytes,
                               inc header */
} ASYNC_MESSAGE_HEADER;
typedef struct tagSubMsgHeader {
    UI32 uiSubMsgType;      /* sub message type in
                               SUB_MESSAGE_TYPE */
    UI32 uiSubMsgOp;        /* sub message operation */
    UI32 uiLogicAddress;    /* logical address */
    UI32 uiAddressOffset;   /* offset to the logical address */
    UI32 uiDataSizeBytes;   /* size in bytes for sub message
                               data section */
} HOST_SUB_MESSAGE_HEADER;
typedef struct tagSubMsgHeader {
    UI32 uiSubMsgType;      /* sub message type in
                               SUB_MESSAGE TYPE */
    UI32 uiStatusId;        /* status Id */
    UI32 uiLogicAddress;    /* logical address */
    UI32 uiAddressOffset;   /* offset to the logical address */
    UI32 uiDataSizeBytes;   /* size in bytes for sub message
                               data section */
} SCANNER SUB_MESSAGE_HEADER;
typedef enum {
    kUspOk,                 /* operation complete
                               successfully */
    kUspMsgExist,           /* message already created */
    kUspInvalidParameter,   /* wrong input parameters */
    kUspExceedTotalMsgs,    /* exceed the total messages * 
} USP_STATUS;
typedef struct {
    USP_MESSAGE_TYPE msgType,
    UI32 numberSubMessages,
    UI32 ultrasoundStateID
} APPLICATION_MESSAGE_HEADER,
*PAPPLICATION_MESSAGE_HEADER;
typedef struct {
    void *pBuf;             /* start address of this
                               message buffer */
    UI32 bufSize;           /* size in bytes of this message
                               buffer */
} USP_MESSAGE_DESC * PUSP_MESSAGE _DESC;
typedef struct {
    UI32 uiFrameType;       /* received frame type */
#define B_FRAME        0x0
#define COLOR_FRAME    0x1
#define M_FRAME        0x2
#define DOPPLER_FRAME  0x4
    UI32 ultrasoundStateID; /* current ultrasound state id */
    UI32 uiFrameId;         /* current frame id */
    US8 pFrameData;         / * frame data pointer */
} USP_FRAME_DESC, *PUSP_FRAME_DESC;
```

The USP APIs described herein represent exemplary functions that provide the services to construct and interpret USP asynchronous messages for both host and scanner software. The USP APIs receive requests from the application layer program to perform functions related to the construction and interpretation of command and bulk data information, such that ultrasound application programmers for both host and scanner device manufacturers do not need to concern themselves with specific USP formatting issues. Rather, the application programmers may simply use the USP APIs provided herein and other USP APIs that may be developed in accordance with the preferred embodiments. It is to be noted in the present examples, however, that the application layer is responsible for allocating memory for message headers and message data, and is also responsible for sending and receiving messages by calling the UTP layer APIs. However, it is within the scope of the preferred embodiments that the USP layer could also provide intelligent APIs capable of performing memory allocation tasks and UTP layer management tasks on behalf of the application program layer.

USP_STATUS USP_StartConstructMessage ( UI32 uiAsyncMsgType, UI32 ultrasoundStateID, UI32 totalSubMessages, PUSP_MESSAGE_DESC **pppubdBufferDesc);

This API is called by the ultrasound application program to construct a USP asynchronous message. This routine allocates an array to hold the message header, tail and submessage descriptor pointers. It also allocates memory for asynchronous message header, tail and submessage descriptors. The ultrasound application passes asynchronous message type and ultrasoundStateID to initialize the message header. The total number of submessages is used to allocate memory. The application also passes a pointer to the constructed message descriptor array, which will be valid when the message construction is complete.

USP_STATUS USP_AddSubMessage ( UI32 numberOfMessagesAdd, PSUB_MESSAGE_DESC *ppSubMsgArray, PUSP_MESSAGE_DESC **pppubdBufferDesc );

This API is called by the ultrasound application program to add a submessage descriptor list to the asynchronous message body. The application passes the submessage counts and the pointer to the message descriptor array to this routine. If the number of submessages to be added exceeds the total number of sub messages passed by calling StartConstructMessage( ), an error kUstrExceedTotalMsgs will be returned.

USP_STATUS USP_EndConstructMessage ( PUSP_MESSAGE_DESC **pppubdBufferDesc);

This API is called by the ultrasound application program to signal the end of message construction. The pppubd- BufferDesc is initialized with the valid pointer to the message descriptor array. The pointer can be passed to the UTP layer send API, supra, to send an asynchronous message.

USP_STATUS USP_FreeMessageBuf( PUSP_MESSAGE_DESC **pppubdBufferDesc);

This API is called by the ultrasound application program to free memory, which is allocated during the message construction. The application should call this routine after the message is sent by the UTP layer send API.

USP_STATUS USP_GetApplMessage ( PUSP_MESSAGE_DESC pubdBufferDesc, PAPPLICATION_MESSAGE pApplMsg);

This API is called by the ultrasound application program to retrieve an application message header from a message. The application passes pubdBufferDesc, which is received by calling UTP_Receive( ). The application allocates the memory for the ApplMsg data structure.

USP_STATUS USP_GetSubMessage ( UI32 indexSubMessage, UC8 *pBufMsg, UC8 **pBufSubMsg);

This API is called by the ultrasound application program to retrieve a sub message from asynchronous message body. The message is specified by indexSubMessage and the message is returned through pBufMsg. The pBufSubMsg indicates from which the sub message should be retrieved. The message header and data are in original message buffer so that the application does not need to allocate memory before calling this routine.

USP_STATUS USP_GetFrameDesc( PUSP_FRAME_DESC pubdFrameDesc, US8 pReceiveFrame);

This API is called by the ultrasound application program to retrieve a frame descriptor from a frame of received data. The application passes pubdFrameDesc, which is a data structure allocated by application and a received data frame pointer. The frame descriptor is filled in by fetching parameters from received data frame header.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments are not intended to limit their scope, which is limited only by the scope of the claims set forth below.

What is claimed is:

1. A computer program product for use in a plurality of ultrasound devices, the plurality of ultrasound devices being coupled to an ultrasound information bus for allowing communications therebetween according to a high-speed packetized serial bus protocol, each ultrasound device having a lower protocol layer for receiving and sending packets using said high-speed packetized serial bus protocol, each ultrasound device having an application layer for performing an ultrasound application function, said computer program product comprising:

computer code for receiving a request from the application layer to communicate with another ultrasound device;

computer code for establishing a connection-oriented communication session with the other ultrasound device through the lower protocol layer across the ultrasound information bus; and computer code for transferring ultrasound information between the application layer and the other ultrasound device during said communication session, said ultrasound information comprising bulk image data requiring real-time transfer, said ultrasound information further comprising command data, wherein said bulk image data is transferred over an isochronous channel of said connection-oriented communication session and said command data is transferred over an asynchronous channel of said connection-oriented communication session;

whereby any of a variety of different ultrasound devices having application layers compatible with said computer program product are capable of communications therebetween when coupled to the ultrasound information bus.

2. The computer program product of claim 1, further comprising computer code for terminating said connection-oriented communication session responsive to a command received from the application layer.

3. The computer program product of claim 2, further comprising:

computer code for forming a bulk image frame responsive to receiving bulk image data from the application layer;

computer code for encapsulating the bulk image frame into one or more connection-oriented protocol packets; and computer code for submitting said connection-oriented protocol packets to the lower layer protocol for transmission to the other ultrasound device.

4. The computer program product of claim 3, further comprising:

computer code for receiving connection-oriented protocol packets from the other ultrasound device through the lower layer protocol;

computer code for unpacking bulk image frames from the connection-oriented protocol packets; and computer code for transferring the bulk image data to the application layer.

5. The computer program product of claim 4, further comprising computer code for forming a bulk image data port, wherein bulk image data is transferred between the ultrasound devices in connection-oriented communication sessions between their bulk image data ports.

6. The computer program product of claim 5, wherein said bulk image data is selected from the group consisting of: B-mode image data, M-mode image data, Color Doppler image data, spectral Doppler image data, and ECG image data.

7. The computer program product of claim 2, further comprising:

computer code for forming a command frame responsive to receiving command data from the application layer;

computer code for encapsulating the command frame into one or more connection-oriented protocol packets; and computer code for submitting said connection-oriented protocol packets to the lower layer protocol for transmission to the other ultrasound device.

8. The computer program product of claim 7, further comprising:

computer code for receiving connection-oriented protocol packets from the other ultrasound device through the lower layer protocol;

computer code for unpacking command frames from the connection-oriented protocol packets; and computer code for transferring the command data to the application layer.

9. The computer program product of claim 8, further comprising computer code for forming a command port, wherein command data is transferred between the ultrasound devices in connection-oriented communication sessions between their command data ports.

10. The computer program product of claim 9, wherein said command data is selected from the group of command types consisting of: open port, load code at logical address, run, status request, status request response, reset, reset acknowledge, stop, and close port.

11. The computer program product of claim 10, said ultrasound devices including a scanning device and a host device, said scanning device generating image data in accordance with intrinsic parameters that are included within each bulk data frame, said scanning device also generating image data in accordance with extrinsic parameters that are not included within each bulk data frame, further comprising:

at the scanning device, computer code for attaching an ultrasound state identifier to each bulk image frame, said ultrasound state identifier being associated with a corresponding set of extrinsic parameters; and at the host, computer code for receiving the ultrasound state identifier from the bulk image frame and transferring it to the application layer for association with the bulk image data within that frame;

whereby the host device may properly interpret the bulk image data using (a) the intrinsic parameters included with the bulk image data, and (b) using extrinsic parameters that may be derived from knowledge of the ultrasound state identifier;

and whereby the extrinsic parameters themselves are not required to be included with each bulk image frame.

12. The computer program product of claim 11, wherein changes in the extrinsic parameters are caused by the host device, and wherein new extrinsic parameters and corresponding new ultrasound state identifiers are communicated to the scanning device across the asynchronous command connection.

13. The computer program product of claim 12, further comprising computer code for forming a broadcast port, said broadcast port for allowing the host device to broadcast, upon change in the extrinsic parameters, the new extrinsic parameters and corresponding new ultrasound state identifier to broadcast ports of the scanning device and other ultrasound devices coupled to the ultrasound information bus.

14. The computer program product of claim 13, wherein successive ultrasound state identifiers form a linear numerical progression.

15. The computer program product of claim 13, wherein successive ultrasound state identifiers form a random numerical sequence.

16. The computer program product of claim 13, wherein said extrinsic parameters include parameters selected from the group consisting of: pulse repetition frequency, magnification factor, and Color Doppler region of interest.

17. A method for transferring ultrasound information between a first ultrasound device and a second ultrasound device, the ultrasound information comprising command data and bulk image data, comprising the steps of:

forming an asynchronous virtual connection between a command port of said first ultrasound device and a command port of said second ultrasound device;

forming an isochronous virtual connection between a bulk image data port of said first ultrasound device and a bulk image data port of said second ultrasound device, wherein said asynchronous and isochronous virtual connections are formed in a common high-speed serial link between said first and second ultrasound devices according to a high-speed packetized serial bus protocol;

transmitting command data across said asynchronous virtual connection; and transmitting bulk image data across said isochronous virtual connection.

18. The method of claim 17, the bulk image data being organized into frames by the second ultrasound device for transmission to the first ultrasound device, the second ultrasound device creating the bulk image data in accordance with (a) intrinsic parameters that are included within each bulk data frame and (b) extrinsic parameters that are not included within each bulk image frame, said first ultrasound device requiring both said intrinsic and extrinsic parameters in order to process the bulk image data, the method further comprising the steps of:

at the second ultrasound device, attaching an ultrasound state identifier to each bulk image frame, said ultrasound state identifier being associated with a corresponding set of extrinsic parameters; and at the first ultrasound device, using said ultrasound state identifier to derive the extrinsic parameters associated with each bulk image frame;

whereby the extrinsic parameters themselves are not required to be included with each bulk image frame.

19. The method of claim 18, wherein changes in the extrinsic parameters are caused by the first ultrasound device, and wherein new extrinsic parameters and corresponding new ultrasound state identifiers are communicated to the second ultrasound device across the asynchronous virtual connection.

20. The method of claim 19, further comprising the steps of:

at said first ultrasound device, storing the current extrinsic parameters and corresponding ultrasound state identifier;

upon a change of extrinsic parameters at said first ultrasound device, also storing the new extrinsic parameters and corresponding new ultrasound state identifier;

at said first ultrasound device, comparing the ultrasound state identifiers of the incoming bulk image frames to the stored ultrasound state identifiers and using the corresponding extrinsic parameters to process the bulk image data;

whereby any bulk image frames that were pending transmission prior to the change in extrinsic state are properly associated with the correct extrinsic parameters at the first ultrasound device, thereby achieving synchronization of the first and second ultrasound devices.

21. The method of claim 20, wherein successive ultrasound state identifiers form a linear numerical progression.

22. The method of claim 20, wherein successive ultrasound state identifiers form a random numerical sequence.

23. The method of claim 20, wherein the extrinsic parameters include parameters selected from the group consisting of: pulse repetition frequency, magnification factor, and Color Doppler region of interest.

24. A method for ultrasound information processing in a modular ultrasound system having a host, a scanner, and an intermediate processor, comprising the steps of:

forming a first asynchronous virtual connection between a first command port of the host and a command port of the scanner, said first asynchronous virtual connection being formed in a first high-speed serial link connecting said host and said scanner according to a high-speed packetized serial bus protocol;

forming a second asynchronous virtual connection between a second command port of the host and a command port of the intermediate processor, said second asynchronous virtual connection being formed in a second high-speed serial link connecting said host and the intermediate processor according to said high-speed packetized serial bus protocol;

forming a first isochronous virtual connection between a bulk image data port of the scanner and a first bulk image data port of the intermediate processor, said first isochronous virtual connection being formed in said first and second high-speed serial links across said host;

forming a second isochronous virtual connection between a second bulk image data port of the intermediate processor and a bulk image data port of the host, said second asynchronous virtual connection being formed in said second high-speed serial link;

transmitting command data across said first and second asynchronous virtual connections;

transmitting bulk image data from the scanner to the intermediate processor across said first isochronous virtual connection;

processing said bulk image data at the intermediate processor; and subsequent to processing said bulk image data, transmitting said bulk image data from the intermediate processor to the host across said second isochronous virtual connection.

25. The method of claim 24, said bulk image data being organized into frames for transmission across said first and second isochronous virtual connections, the scanner creating bulk image data in accordance with (a) intrinsic parameters that are included within each bulk data frame and (b) extrinsic parameters that are not included within each bulk image frame, said host and said intermediate processor each requiring said intrinsic and extrinsic parameters in order to process said bulk image data, the method further comprising the steps of:

at the scanner, attaching an ultrasound state identifier to each bulk image frame, said ultrasound state identifier being associated with a corresponding set of extrinsic parameters, and transmitting said bulk image frame to the intermediate processor;

at the intermediate processor, using said ultrasound state identifier from each arriving bulk image frame to derive the corresponding extrinsic parameters for use in processing said bulk image frames;

at the intermediate processor, transmitting the bulk image frames to the host with their respective ultrasound state identifiers;

at the host, using both (a) the intrinsic parameters in each arriving bulk data frame and (b) extrinsic parameters derived from the ultrasound state identifier of each arriving bulk data frame to process said bulk data frame.

26. The method of claim 25, wherein the extrinsic parameters include parameters selected from the group consisting of: pulse repetition frequency, magnification factor, and Color Doppler region of interest.

27. The method of claim 26, the extrinsic parameters being subject to changes caused by events at the host, wherein upon generation of new extrinsic parameters at the host, said new extrinsic parameters and a corresponding new ultrasound state identifier are communicated from the host to the scanner and to the intermediate processor across said first and second asynchronous virtual connections, respectively.

28. The method of claim 27, further comprising the steps of:

at the host and the intermediate processor, storing the extrinsic parameters and corresponding ultrasound state identifier;

upon said change of said extrinsic parameters at the host, storing said new extrinsic parameters and said corresponding new ultrasound state identifier at the host and the intermediate processor;

at the host and the intermediate processor, using the ultrasound state identifiers of arriving bulk image frames to locate the extrinsic parameters corresponding to that bulk image frame; and at the host and the intermediate processor, processing that bulk image frame using said located extrinsic parameters;

whereby any bulk image frames which were pending transmission at the scanner or the intermediate processor prior to said change in extrinsic parameters are properly associated with the correct extrinsic parameters for processing, whereby synchronization of the host, the intermediate processor, and the scanner is achieved.

29. The method of claim 26, the extrinsic parameters being subject to changes caused by events at the host, wherein upon generation of new extrinsic parameters at the host, said new extrinsic parameters and a corresponding new ultrasound state identifier are communicated from the host to the scanner across said first asynchronous virtual connection and said new extrinsic parameters and corresponding new ultrasound state identifier are communicated from the scanner to the intermediate processor across a third asynchronous virtual circuit formed between a second command port of the scanner and a second command port of the intermediate processor.

30. The method of claim 26, the extrinsic parameters being subject to changes caused by events at the host, wherein upon generation of new extrinsic a parameters at the host, said new extrinsic parameters and a corresponding new ultrasound state identifier are broadcasted from a broadcast port of the host to broadcast ports on each of said scanner and said intermediate processor.

31. A medical diagnostic ultrasound system comprising:

two or more ultrasound devices each having a respective application layer program and a respective lower protocol layer program;

an ultrasound information bus coupled with the ultrasound devices for transfer of ultrasound information between the devices over the bus;

wherein the application layer programs control operations of the respective ultrasound devices and the lower protocol layer programs control transfers of ultrasound information between the respective devices and the bus; and an ultrasound information exchange protocol program receiving communication requests from respective application layer programs sent via the bus and, in response, causing a communication session to commence between a requesting and requested ones of said ultrasound devices, said communication session comprising the transfer of ultrasound information between the requesting and requested devices via the ultrasound information bus and the lower protocol layer programs of the requesting and requested devices;

wherein ultrasound devices with respective application layer programs and lower protocol layer programs can be added to or removed from the system without requiring modification of the devices that remain coupled with the information bus, wherein said ultrasound information comprises bulk image data requiring real-time transfer that is transferred using an isochronous channel of the bus; and wherein said ultrasound information further comprises command data that is transferred over an asynchronous channel of the bus.

32. A system as in claim 31 in which:

said ultrasound devices include a scanning device and a host device;

said scanning device generating image data in accordance with intrinsic parameters that are included within bulk data frames and also generating image data in accordance with extrinsic parameters that are not included within each of the bulk data frames, said system further comprising:

at the scanning device, computer code for attaching an ultrasound state identifier to each bulk image frame, said ultrasound state identifier being associated with a corresponding set of extrinsic parameters; and at the host, computer code for receiving the ultrasound state identifier from the bulk image frame and transferring it to the application layer for association with the bulk image data within that frame;

said host device interpreting the bulk image data using (a) the intrinsic parameters included with the bulk image data, and (b) extrinsic parameters that may be derived from knowledge of the ultrasound state identifier.

33. A system as in claim 32 in which changes in the extrinsic parameters are caused by the host device, and new extrinsic parameters and corresponding new ultrasound state identifiers are communicated to the scanning device across an asynchronous command connection.

34. A system as in claim 32 in which said extrinsic parameters include parameters selected from the group consisting of: pulse repetition frequency, magnification factor, and Color Doppler region of interest.

35. A medical diagnostic method using ultrasound comprising:

coupling two or more ultrasound devices, each having a respective application layer program and a respective lower protocol layer program, with an ultrasound information bus for transfer of ultrasound information between the devices over the bus;

wherein the application layer programs control operations of the respective ultrasound devices and the lower protocol layer programs control transfers of ultrasound information between the respective devices and the bus; and using an ultrasound information exchange protocol program receiving communication requests from respective application layer programs sent via the bus and, in response, causing a communication session to commence between a requesting and requested ones of said ultrasound devices, said communication session comprising the transfer of ultrasound information between the requesting and requested devices via the ultrasound information bus and the lower protocol layer programs of the requesting and requested devices;

wherein ultrasound devices with respective application layer programs and lower protocol layer programs can be added to or removed from the system without requiring modification of the devices that remain coupled with the information bus;

wherein said ultrasound information comprises bulk image data requiring real-time transfer that is transferred using an isochronous channel of the bus; and wherein said ultrasound information further comprises command data that is transferred over an asynchronous channel of the bus.

36. A method as in claim 35 in which:

said ultrasound devices include a scanning device and a host device;

said scanning device generating image data in accordance with intrinsic parameters that are included within bulk data frames and also generating image data in accordance with extrinsic parameters that are not included within each of the bulk data frames, said method further comprising:

at the scanning device, using computer code attaching an ultrasound state identifier to each bulk image frame, said ultrasound state identifier being associated with a corresponding set of extrinsic parameters; and at the host, using computer code receiving the ultrasound state identifier from the bulk image frame and transferring it to the application layer for association with the bulk image data within that frame;

said host device interpreting the bulk image data using (a) the intrinsic parameters included with the bulk image data, and (b) extrinsic parameters that may be derived from knowledge of the ultrasound state identifier.

37. A system as in claim 36 in which changes in the extrinsic parameters are caused by the host device, and new extrinsic parameters and corresponding new ultrasound state identifiers are communicated to the scanning device across an asynchronous command connection.

38. A system as in claim 36 in which said extrinsic parameters include parameters selected from the group consisting of: pulse repetition frequency, magnification factor, and Color Doppler region of interest.

* * * * *